US007410642B2

(12) United States Patent
Harley et al.

(10) Patent No.: US 7,410,642 B2
(45) Date of Patent: Aug. 12, 2008

(54) ASSAYS AND THERAPIES FOR LATENT VIRAL INFECTION

(75) Inventors: John B. Harley, Oklahoma City, OK (US); Judith Ann James, Edmond, OK (US); Kenneth M. Kaufman, Oklahoma City, OK (US)

(73) Assignee: Oklahoma Medical Research Foundation, Oklahoma City, OK (US)

( * ) Notice: Subject to any disclaimer, the term of this patent is extended or adjusted under 35 U.S.C. 154(b) by 0 days.

(21) Appl. No.: 11/405,355

(22) Filed: Apr. 17, 2006

(65) Prior Publication Data

US 2006/0257427 A1 Nov. 16, 2006

Related U.S. Application Data

(62) Division of application No. 10/646,132, filed on Aug. 22, 2003, now Pat. No. 7,078,173, which is a division of application No. 09/718,693, filed on Nov. 22, 2000, now Pat. No. 6,642,008.

(60) Provisional application No. 60/167,212, filed on Nov. 24, 1999.

(51) Int. Cl.
*A61K 39/12* (2006.01)
(52) U.S. Cl. .................. 424/204.1; 424/130.1; 435/345
(58) Field of Classification Search ................. 435/435, 435/6; 424/204.1, 130.1
See application file for complete search history.

(56) References Cited

U.S. PATENT DOCUMENTS

| 4,244,946 A | 1/1981 | Rivier et al. | 514/15 |
|---|---|---|---|
| 4,305,872 A | 12/1981 | Johnston et al. | 530/330 |
| 4,316,891 A | 2/1982 | Guillemin et al. | 514/11 |
| 4,675,382 A | 6/1987 | Murphy | 530/350 |
| 4,792,525 A | 12/1988 | Ruoslahti et al. | 435/402 |
| 5,637,454 A | 6/1997 | Harley | 435/5 |
| 5,861,240 A * | 1/1999 | Ganem et al. | 435/5 |
| 5,906,820 A | 5/1999 | Bacha | 424/183.1 |

FOREIGN PATENT DOCUMENTS

| WO | WO 98/30586 | 7/1998 |
|---|---|---|
| WO | WO 99/02550 | 1/1999 |

OTHER PUBLICATIONS

Rowe et al. Journal of General Virology, 1987, vol. 68, pp. 1575-1586.*
Meij et al. The Journal of Infectious Diseases, May 1999, vol. 179, pp. 1108-1115.*
Adelstein et al., "Radiobiologic implications of the microscopic distribution of energy from radionuclides," *Nucl. Med. Biol.*, 14:165-169, 1987.
Alford, Antiviral agents and viral diseases of man, 2nd ed. Raven Press: New York, pp. 433-486, 1984.
Alspaugh et al., "Elevated levels of antibodies to Epstein-Barr virus antigens in sera and synovial fluids of patients with rheumatoid arthritis," *J. Clin. Invest.*, 67:1134-1140, 1981.
Alspaugh et al., "Serum antibody in rheumatoid arthritis reactive with a cell-associated antigen. Demonstration by precipitation and immunofluorescence," *Arthr. Rheum.*, 19:711-719, 1976.
Ashley et al., "Detection of asymptomatic herpes simples virus infections after vaccination," *J. Virol.*, 61:253-258, 1987.
Babcock et al., "Epstein-barr virus-infected resting memory B cells, not proliferating lymphoblasts, accumulate in the peripheral blood of immunosuppressed patients," *J. Exp. Med.*, 190:567-576, 1999.
Barnes, *J. Pharma Weekly*, 1:11, 1995.
Bell et al., "Antibody to rheumatoid arthritis associated nuclear antigen (RANA) in familial rheumatoid arthritis," *J. Rheumatol.*, 11:277-281, 1984.
Bray et al., "Antibodies against Epstein-Barr Nuclear Antigen (EBNA) in Multiple Sclerosis CSF, and two pentapeptide sequence identities between EBNA and Myelin basic protein," *Arch. Neur.*, 42:1798-1804, 1992.
Bray et al., "Antibodies against Epstein-Barr nuclear antigen (EBNA) in multiple sclerosis CSF< and two pentapeptide sequences identities between EBNA and myelin basic protein," *Arch. Neur.*, 40:406-408, 1983.

(Continued)

*Primary Examiner*—Ali R. Salimi
(74) *Attorney, Agent, or Firm*—Fulbright & Jaworski, LLP

(57) ABSTRACT

Compositions that bind viral proteins that are specifically expressed during the latent stage of the viral life cycle are disclosed. These compositions bind the latent viral proteins while the viral proteins are expressed in their cellular host, and provide a means for targeting cells that harbor latent virus. In a preferred embodiment the compositions are antibodies which bind the extracellular region of the latent viral protein, most preferably LMP-2A, an EBV latent protein, which are conjugated to a diagnostic or cytotoxic agent or immobilized to a solid support for removal of the infected cells. These antibodies are capable of distinguishing cells expressing EBV DNA from cells which are not expressing EBV DNA. Compositions that can be used to elicit production of these antibodies, or as a vaccine, are also disclosed. Methods for generating diagnostic or cytotoxic reagents and vaccines based on the viral epitopes that identify cells harboring latent virus are also disclosed. The antibody conjugates can be used in diagnostic assays to identify cells expressing latent viral protein and people who are harboring latent viral particles. The antibody conjugates can also be used to remove the infected cells or to kill the infected the cells. Alternatively, or in addition, the viral proteins or portions thereof can be used as a vaccine to induce an immune reaction by the host to kill the infected cells. These methods can be used to detect or treat patients harboring latent viruses like EBV and who are at risk of developing a disease such as an autoimmune disease like systemic lupus erythematosus (SLE) and rheumatoid arthritis (RA).

7 Claims, No Drawings

OTHER PUBLICATIONS

Browning et al., "Studies on the differing effects of tumor necrosis factor and lymphotoxin on the growth of several human tumor lines," *J. Immunol.*, 143:1859-1867, 1989.

Calderwood et al., "Nucleotide sequence of the Shiga-like toxin genes of *Escherichia coli*," *Proc. Natl. Acad. Sci. USA*, 84:4364-4368, 1987.

Catalano et al., "Antibodies of Epstein-Barr virus-determined antigens in normal subjects and in patients with seropositive rheumatoid arthritis," *Proc. Natl. Acad. Sci. USA*, 76:5825-5828, 1979.

Chen et al., "Production of mulitmeric forms of CD4 through sugar-based cross-linking strategy," *J. Biol. Chem.*, 266:18237-18243, 1994.

Colombatti et al., Cloned fragment of diphtheria toxin linked to T cell-specific antibody identifies regions of B chain active in cell entry, *J. Biol. Chem.*, 261:3030-3035, 1986.

Dalldorf et al., "The lymphomas of Brazilian children," *J. Am. Med. Assn.*, 208:1365-1368, 1969.

Deacon et al., "Detection of Epstein-Barr virus antigens and DNA in major and minor salivary glands using immunocytochemistry and polymerase chain reaction: possible relationship with Sjogren's Syndrome," *J. Pathol.*, 163:351-360, 1991.

Deacon et al., "Frequency of EBV DNA detection in Sjogren's Syndrome," *Am. J. Med.*, 92:453-454, 1992.

Debrus et al., "Varicella-zoster virus gene 63 encodes an immediate-early protein that is abundantly expressed during latency," *J. Virol.*, 69:3240-3245, 1995.

Dedrick et al., "Pharmacokinetic rationale for peritoneal drug administration in the treatment of ovarian cancer," *Cancer Treat Rep.*, 62:1-11, 1978.

Deleers et al., "Localization in diphtheria toxin fragment B of a region that induces pore formation in planar lipid bilayers at low pH," *FEBS Lett.*, 160:82-86, 1983.

Diener et al., "Specific immunosuppression by immunotoxins containing daunomycin," *Science*, 231:148-150, 1986.

Digard et al., "Functional analysis of the herpes simplex virus UL42 protein," *J. Virol.*, 67:1159-1168, 1993.

Dittmer et al., "A cluster of latently expressed genes in Kaposi's sarcoma-associated herpes virus," *J. Virol.*, 72:8309-8315, 1998.

Donahue et al., "The incidence of herpes zoster," *Arch. Int. Med.*, 155:1605-1609, 1995.

Elek et al., "Development of a vaccine against mental retardation caused by cytomegalovirus infection in utero," *Lancet*, 1:1-5, 1974.

Ertl et al., "Physical and functional interation of human cytomegalovirus DNA polymerase and its accessory protein (ICP36) expressed in insect cells," *J. Virol.*, 66:4126-4133, 1992.

Ferrel et al., "Seroepidemiologial study of relationships between Epstein-Barr virus and rheumatoid arthritis," *J. Clin. Invest.*, 67:681-687, 1981.

Finerty et al., "Immunization of Cottontop Tamarins and rabbits with a candidate vaccine against the Epstein-Barr virus based on the major viral envelope Glycoprotein gp340 and Alum," *Vaccine*, 12:1180-1184, 1994.

Finerty et al., "Protective immunization against Epstein-Barr virus-induced disease in Cottontop Tamarins using the virus envelope glycoprotein gp340 produced fro a Bovine Papillomavirus expression vector," *J. Gen. Virol.*, 73:449-453, 1992.

Fox et al., "Detection of Epstein-Barr virus-associated antigens in DNA in salivary glands biopsies from patients with Sjogren's Syndrome," *J. Immunol.* 137:3162-3168, 1986.

Fox et al., "Potential role of Epstein-Barr Virus in Sjogren's Syndrome and Rheumatoid Arthritis," *J. Rheumatol.*, 19:18-24, 1992.

Fox, "Sjogren's Syndrome," *Current Opin. Rheum.*, 7:409-416, 1995.

Glassy et al., "Immunodetection of cell-bound antigens using both mouse and human monoclonal antibodies," *J. Immunol. Methods*, 81:115, 1985.

Goodrich et al., "Ganciclovir prophylaxis to prevent cytomegalovirus disease after allogeneic marros transplant," *Ann. Intern. Med.*, 118:173-178, 1993.

Gray et al., "Cloning, nucleotide sequence, and expression in *Escherichia coli* of the exotoxin A structural gene of *Pseudomonas aeruginosa*," *Proc. Natl. Acad. Sci. USA*, 81:2645-2649, 1984.

Greenwood et al., "The Preparation of I-131-Labelled Human Growth Hormone of High Specific Radioactivity," *Biochem J.*, 89:114-123, 1963.

Griffiths et al., "Direct radiolabeling of monoclonal antibodies with generator-produced rhenium-188 for radioimmunotherapy: labeling and animal biodistribution studies," *Cancer Res.*, 51:4594-4602, 1991.

Gu et al., "First EBV vaccine trial in human using recombinant vaccinia virus expressing the major membrane antigen," *Dev. Biol. Stand.*, 84:171-177, 1995.

Gutierrez et al., "Switching viral latency to viral lysis: a novel therapeutic approach for Epstein-Barr Virus-Associated Neoplasia," *Cancer Res.*, 56:969-972, 1996.

Haahr et al., "A putative new retrovirus associated with multiple sclerosis and the possible involvement of the Epstein-Barr virus in this disease," *Ann. N.Y. Acad. Sci.*, 724:148-156, 1996.

Halpern et al., "Distribution of radiolabeled human and mouse monoclonal IgM antibodies in murine models," *J. Nucl. Med.*, 29:1688-1696, 1988.

Harley and James, "Epstein-Barr virus infection may be an environmental risk factor for systemic lupus erythematosus in children and teenagers," *Arth. Rheum.*, 42:172-1783, 1999.

Heslop et al., "Long-term restoration of immunity against Epstein-Barr virus infection by adoptive transfer of gene-modified virus specific T lymphocytes," *Nature Med.*, 2:551-555, 1996.

Hiskey, "Sulfhydryl group protection in peptide synthesis," *Peptides*, 3:137, 1981.

Ho, Cytomegalovirus, biology and infection: current topics in infectious disease, Plenum Press: New York, pp. 105-118, 1982.

Hoch et al., "Channels formed by botulinum, tetanus, and diphtheria toxins in planar lipid bilayers: relevance to translocation of proteins across membranes," *Proc. Natl. Acad. Sci. USA*, 82:1692-1696, 1985.

Hwang et al., "Functional domains of *Pseudomonas exotoxin* identified by deletion analysis of the gene expressed in *E. coli*," *Cell*, 48:129-136, 1987.

Inou et al., "Analysis of antibody titers to Epstein-Barr Virus Nuclear Antigens in Sera of patients with Sjogren's syndrome and with Rheumatoid Arthritis," *J. Infect. Dis.*, 164:22-28, 1991.

Ishii et al., "Cycloheximide-induced apoptosis in Burkitt Lymphoma (BJA-B) Cells with and without Epstein-Barr Virus infection," *Immunol. Cell Biol.*. 73:463-468, 1995.

James and Harley, "Linear epitope mapping of an Sm B/B' polypeptide," *J. Immunol.*, 148:2074-2079, 1992.

James et al., "An increased prevalence of Epstein-Barr virus infection in young patients suggests a possible etiology for systemic lupus erythematosus," *J. Clin. Invest.*, 100:3019-3026, 1997.

James et al., "Epstein Barr virus nuclear antigen-1 immune response differences between systematic lupus erythematosus patients and normal controls," *Athr. Rheum.*, 41:S308, 1998.

James et al., "Immunoglobulin epitope spreading and autoimmune disease after peptide immunization: Sm B/B'-derived PPPGMRPP and PPPGIRGP induce spliceosome autoimmunity," J. Exp. Med., 181:453-461, 1995.

Ji, "Bifunctional reagents," *Met. Enzymol.*, 91:580-609, 1983.

Kahan et al., "Different defects of T cell regulation of Epstein-Barr virus-incuded B cell activation in rheumatoid arthritis," *Arthr. Rheum.* 28:961-960, 1985.

Karameris et al., *Clin. Exp. Rheum.*, 10:327-332, 1992.

Khanna et al., "Peptide transporter (TAP-1 and TAP-2)-independent endogenous processing of Epstein-Barr virus (EBV) latent membrane protein 2A: implications for cytotoxic T-lymphocyte control of EBV-associated malignancies," *J. Virol.*, 70:5357-5362, 1996.

Kimura et al., "Establishment of anti-Epstein-Barr virus (EBV) cellular immunity by adoptive transfer of virus-specific cytotoxic T lymphocytes from and HLA-matched sibling to a patient with severe chronic active EBV infection," *Clin. Exp. Immunol.*, 103:192-298, 1996.

Kitagawa et al., "Detection of antibodies to the Epstein-Barr virus nuclear antigens in the sera from patients with systemic lupus erythematosus," *Immunol. Lett.*, 17:249-252, 1988.

Kohler and Milstein, "Continuous cultures of fused cells secreting antibody of predefined specificity," *Nature*, 256:495-497, 1975.

Kohler and Milstein, "Derivation of specific antibody-producing tissue culture and tumor lines by cell fusion," *Eur. J. Immunol.*, 6:511-519, 1976.

Koide et al., "Spontaneous establishment of an Epstein-Barr virus-infected fibroblast line from the synovial tissue of a rheumatoid arthritis patient," *J. Virol.*, 71:2478-2481, 1997.

Kondo and Yamanishi, "The role of human cytomegalovirus, human herpesvirus 6 and 7 latent transcripts," *24th International Herpesvirus Workshop*, Jul. 17-23 (Mass. Inst. Tech.) Abst. 1.016, 1999.

Koyama et al., "Preparation of maleimide chelating agents for radiodiagnosis," *Chem. Abstr.*, 120:217-262, 1994.

Krause and Strauss, "Herpesvirus vaccines development, controversies, and applications," *Infect. Dis. Clin. N.A.*, 13:61-81, 1999.

Larsen et al., "Epstein-Barr Nuclear Antigen and Viral Capsid Antigen Antibody Titers in Multiple Sclerosis," *Neurology*, 35:435-438, 1985.

Lazarovits et al., "Anti-B cell antibodies for the treatment of monoclonal Epstein-Barr virus-induced lymphoproliferative syndrome after multivisceral transplantation," *Clin. Invest. Med.*, 17:621-625, 1994.

Lennette et al., "Antibodies to LMP2A/2B in EBV-carrying malignancies," *Eur. J. Cancer*, 31:1875-1878, 1995.

Levitskaya, "Inhibition of Antigen Processing by the Internal Repeat Region of the Epstein-Barr Virus Nuclear Antigen-1," *Nature*, 375:685-688, 1995.

Longnecker and Kieff, "A second Epstein-Barr virus membrane protein (LMP2) is expressed in latent infection and colocalizes with LMP1," *J. Virol.*, 64:2319-2326, 1990.

Mahalingam et al., "Expression of protein encoded by varicella-zoster virus open reading frame 63 in latently infected human ganglionic neurons," *Proc. Natl. Acad. Sci. USA*, 93:2122-2124, 1996.

Maitland, "Frequency of EBV-DNA detection in Sjogren's Syndrome," *Am. J. Med.*, 96:97, 1994.

Mariette et al., "Detection of Epstein-Barr virus DNA by in situ hybridization and polymerase chain reaction in salivary gland biopsy specimens from patients with Sjogren's syndrome," *Am. J. Med.*, 90:286-294, 1991.

Markman, "Intraperitoneal chemotherapy," *Semin. Oncol.*, 248-254, 1991.

Massen et al., "Synthesis and application of two reagents for the introduction of sulfhydryl groups into proteins," *Eur. J. Biochem.*, 164:32, 1983.

Means et al., Chemical modification of proteins, Holden-Day: San Francisco, pp. 105-110, 1971.

Meares et al., "Conjugation of antibodies with bifunctional chelating agents: isothiocyanate and bromoacetamide reagents, methods of analysis, and subsequent addition of metal ions," *Anal. Biochem.*, 142:68-78, 1984.

Meigner et al., "In vitro behavior of genetically engineered herpes simplex viruses R7017 and R7020. II. Studies in immunocompetent and immunosuppressed owl monkeys (*Aotus trivirgatus*)," *J. Infect. Dis.*, 162:312-321, 1990.

Merrifield, "Solid phase peptide synthesis. I. The synthesis of a tetrapeptide," *J. Am. Chem. Soc.*, 85:2149, 1964.

Miyashita et al., "Identification of the site of Epstein-Barr virus persistence in vivo as a resting B cell," *J. Virol.*, 71:4882-4891, 1997.

Mocarski, "Cytomegaloviruses and their replication," In: Fields Virology, 3rd ed. Lippincott-Raven pp. 2447-2480, 1996.

Morgan et al., "Validation of a first-generation Epstein-Barr virus vaccine preparation suitable for human use," *J. Med. Virol.*, 29:74-78, 1989.

Morgan, "Epstein-Barr virus vaccines," *Vaccine*, 10:563-571, 1992.

Morshed et al., "Increased expression of Epstein-Barr virus in primary biliary cirrhosis patients," *Gastroenterol. Jpn.*, 27:751-758, 1992.

Mujoo et al., "Adenoviral-mediated p53 tumor suppressor gene therapy of human ovarian carcinoma," *Oncogene*, 12:1617-1623, 1996.

Murray et al., "Identification of target antigens for the human cytotoxic T cell response to Epstein-Barr virus (EBV): Implications for the immune control of EBV-positive malignancies," *J. Exp. Med.*, 176:157-168, 1992.

Musiani et al., "Comparison of the immune response to Epstein-Barr virus and cytomegalovirus in sera and synovial fluids of patients with rheumatoid arthritis," *Ann. Rheum. Dis.*, 46:837-842, 1987.

Myers et al., "The effects of aromatic and aliphatic maleimide crosslinkers on anti-CD5 ricin immunotoxins," *J. Immunol. Meth.*, 121:129-142, 1989.

Nakabayashi et al., "Antibodies to rheumatoid arthritis nuclear antigen (RANA) in Japanese patients with rheumatoid arthiritis," *Rheumatol. Int.*, 5:61-67, 1985.

Newkirk et al., "Detection of Cytomegalovirus, Epstein-Barr Virus and Herpes Virus-6 in Patients with Rheumatoid Arthritis With or Without Sjogren's Syndrome," *Br. J. Rheum.*, 33:317-322, 1994.

Ng et al., "Anti-RNA antibody: a marker for seronegative and seropositive rheumatoid arthritis," *Lancet*, 1:447-449, 1980.

Oi et al., "Chimeric antibodies," *BioTechniques*, 4:214, 1986.

Pallesen et al., "Expression of Epstein-Barr virus latent gene products in tumour cells of Hodgkin's disease," *Lancet*, 337:320-322, 1991.

Pflugfelder et al., "Amplification of Epstein-Barr Virus Genomic Sequences in Blood Cells, Lacrimal Glands, and Tears from Primary Sjogren's Syndrome Patients," *Ophthalmology*, 97:976-984, 1990.

Pflugfelder et al., "Epstein-Barr virus and the lacrimal gland pathology of Sjogren's syndrome," *Am. J. Pathol.*, 143:49-64, 1993.

Plotkin et al., "Candidate cytomegalovirus strain for human vaccination," *Infect. Immun.*, 12:521-527, 1975.

Plotkin et al., "Protective effects of towne cytomegalovirus vaccine against low-passage cytomegalovirus administered as a challenge," *J. Infect. Dis.* 159: 560-565, 1989.

Plotkin et al., "Vaccines for the prevention of human cytomegalovirus infection," *Rev. Infect. Dis.* 12:827-838, 1990.

Quardi et al., "Preclinical evaluation of intravenously administered 111In- and 90Y-labeled B72.3 immunoconjugate (GYK-DTPA) in beagle dogs," *Nucl. Med. Biol.*, 20:559-570, 1993.

Reusser et al., "Phase I-II trial of foscarnet for prevention of cytomegalovirus infection in autologous and allogeneic marrow transplant recipients," *J. Infect. Dis.*, 166:473-479, 1992.

Rickinson and Kieff, "Epstein-Barr virus," In: Fields Virology, Lippincott-Raven, pp. 2397-2446, 1996.

Rodwell et al., "Site-specific covalent modification of monoclonal antibodies: in vitro and in vivo evaluations," *Proc. Natl. Acad. Sci. USA* 83:3632-3636, 1986.

Rowe et al., "Characterization of the serological response in man to the latent membrane protein and the six nuclear antigens encoded by Epstein-Barr virus," *J. Gen. Virol.*, 69:1217-1228, 1988.

Rowlinson et al., "Antibody-guided localization of intraperitoneal tumors following intraperitoneal or intravenous antibody administration," *Cancer Res.*, 47:6528-6531, 1987.

Sabbatini et al., "Autoantibodies from patients with systemic lupus erythernatosus bind a shared sequence of SmD and Epstein-Barr virus-encoded nuclear antigen EBNA I," *Eur. J. Immunol.*, 23:1146-1152, 1993.

Sadzot-Delvaux and Bentier, "Evaluation of the immune response to Varicella Zoster proteins in the elderly," *24th International Herpes Virus Workshop*, Jul. 17-23 (Mass. Inst. Tech.) Abst. 9.009, 1999.

Sadzot-Delvaux et al., "Recognition of the latency-associated immediate early protein IE63 of varicella-zoster virus by human memory T lymphocytes," *J. Immunol.*, 159:2802, 1997.

Salacinski et al., "Iodination of proteins, glycoproteins, and peptides using a solid-phase oxidizing agent, 1,3,4,6-tetrachloro-3 alpha,6 alpha-diphenyl glycoluril (Iodogen)," *Anal. Biochem.*, 117:136-146, 1981.

Schmidt et al., "Nonresponsiveness to an immunodominant Epstein-Barr virus-encoded cytotoxic T-lymphocyte epitope in nuclear antigen 3A: implications for vaccine strategies," *Proc. Natl. Acad. Sci. USA*, 88:9478-9482, 1991.

Scotet et al., "Frequent enrichment for CD8 T cells reactive against common herpes viruses in chronic inflammatory lesions: towards a reassessment of the physiopathological significance of T cell clonal expansions found in autoimmune inflammatory processes," *Eur. J. Immunol.*, 29:973-985, 1999.

Scotet et al., "T cell response to Epstein-Barr virus transctivators in chronic rheumatoid arthritis," *J. Exp. Med.*, 184:1771-1780, 1996.

Sculley et al., "Reactions of sera from patients with rheumatoid arthritis, systemic lupus erythematosus and infectious mononucleosis to Epstein-Barr virus-induced polypeptides," *J. Gen. Virol.*, 67:2253-2258, 1986.

Singh et al., "Decreased Incidence of Viral Infections in Liver Transplant Recipients—Possible Effects of FK506?," *Digestive Dis. Sci.*, 39:15-18, 1994.

Snoeck et al., Multidisciplinary approach to understanding cytomegalovirus disease, Excerpta Medica, Amsterdam, pp. 269-278, 1993.

Spaete, "A recombinant subunit vaccine approach to HCMV vaccine development," *Transplant Proc.*, 23:90-96, 1991.

Spira, et al., "The identification of monoclonal class switch variants by sib section and an ELISA assay," *J. Immunol. Meth.*, 74:307, 1984.

Steplewski et al., "Isolation and characterization of anti-monosialoganglioside monoclonal antibody 19-9 class-switch variants," *Proc. Natl. Acad. Sci. USA*, 82:8653-8657, 1985.

Straus et al., "NIH conference. Varicella-zoster virus infections. Biology, natural history, treatment, and prevention," *Ann. Int. Med.*, 108:221, 1988.

Sumaya et al., "Increased prevalence and titer of Epstein-Barr virus antibodies in patients with multiple sclerosis," *Ann. Neurol.*, 17:371-377, 1985.

Sun et al., "Chimeric antibodies with 17-1A-derived variable and human constant regions," *Hybridoma*, 5:S17, 1986.

Sundberg et al., "Chelating agents for the binding of metal ions to macromolecules," *Nature*, 250:587-588, 1974.

Takei et al., "Detection of Epstein-Barr virus-encoded small RNA 1 and latent membrane protein 1 in synovial lining cells from rheumatoid arthiritis patients," *Int. Immunol.*, 9:739-743, 1997.

Tan, "The possible role of Epstein-Barr virus in rheumatoid arthritis," *Rev. Inf. Dis.*, 1:997-1006, 1979.

Tateishi et al., "Spontaneous production of Epstein-Barr virus by B lymphoblastoid cell lines obtained from patients with Sjogren's syndrome. Possible involvement of a novel strain of Epstein-Barr virus in disease pathogenesis," *Arthritis Rhuem.*, 36,827-835, 1993.

Thorley-Lawson et al., "Epstein-Barr virus and the B cell: that's all it takes," *Trends in Microbiology*, 4:204-208, 1996.

Toda et al., "Sjogren's syndrome (SS) and Epstein-Barr virus (EBV) reactivation," In: Lacrimal Gland, Tear film, and Dry Eye Syndrome, Plenum Press, New York, pp. 647-650, 1994.

Tsai et al., "Detection of Epstein-Barr virus and cytomegalovirus genome in white blood cells from patients with juvenile rheumatoid arthritis and childhood systemic lupus erythematosus," *Int. Arch. Allergy Immunol.*, 106:235-240, 1995.

Venables et al., "The Response to Epstein-Barr Virus Infection in Sjogren's Syndrome," *J. Autoimmunity*, 2:439-448, 1989.

Venables et al., "Persistence of Epstein-Barr virus in salivary gland biopsies from healthy individuals and patients with Sjogren's syndrome," *Clin. Exp. Immunol.*, 75:359-364, 1989.

Venables et al., "Titers of antibodies to RANA in rheumatoid arthritis and normal sera. Relationship to Epstein-Barr virus infection," *Arthr. Rheum.*, 24:1459-1468, 1981.

Vrisendrop et al., "Radioimmunoglobulin therapy," In: High Dose Cancer Therapy, Williams and Wilkins, Baltimore, pp. 84-123, 1992.

Wagstaff et al., "Aciclovir—A Reappraisal of its Antiviral Activity, Pharmacokinetic Properties and Therapeutic Efficacy," *Drugs*, 47:153-205, 1994.

Wang et al., "Liver toxicity induced by combined external-beam irradiation and readioimmunoglobulin therapy," *Radiat. Res.*, 141:292-302, 1995.

Warner and Carp, "Multiple sclerosis etiology—an Epstein-Barr virus hypothesis," *Med. Hypotheses*, 25:93-97, 1988.

Watson et al., "Certain Properties Make Substances Antigenic," In: Molecular Biology of the Gene, 4$^{th}$ edition, The Benjamin/Cummings Publishing Company, Menlo Park, pp. 836, paragraph 3, 1987.

Whitley, "Herpes Simplex viruses," In: Field's Virology, Lippincott-Raven, pp. 2297-2330, 1996.

Whittingham et al., "Epstein-Barr Virus as an Etiological Agent in Primary Sjogren's Syndrome," *Med. Hypothesis*, 22:373-386, 1987.

Wilbur, "Potential use of alpha emittign radionuclides in the treatment of cancer," *Antibiot. Immunoconjug. Radiopharm.*, 4:85-97, 1991.

Wilson et al., "Association of lymphomatoid granulomatosis with Epstein-Barr viral infection of B lymphocytes and response to interferon-alpha 2b," *Blood*, 87:4531-4537, 1996.

Xie and Snyder, "Two short autoepitopes on the nuclear dot antigen are similar to epitopes encoded by the Epstein-Barr virus," *Proc. Natl. Acad. Sci. USA*, 92:1639-1643, 1995.

Yokochi et al., "High titer of antibody to the Epstein-Barr virus membrane antigen in sera from patients with rheumatoid arthritis and systemic lupus erythematosus," *J. Rheumatol.*,16:1029-1032, 1989.

Yuan et al., "Preparation and application of anti-EBNA 1 monoclonal antibodies," *Chinese J. Microbiol. Immunol.*, 9:198-202, 1989.

Zarling et al., "Herpse simplex virus (HSV)-specific proliferative and cytotoxic T-cell responses in humans immunized with an HSV type 2 glycoprotein subunit vaccine," *J. Virol.* 62:4481-4485, 1988.

\* cited by examiner

SEQUENCE LISTING

```
<160> NUMBER OF SEQ ID NOS: 3

<210> SEQ ID NO 1
<211> LENGTH: 497
<212> TYPE: PRT
<213> ORGANISM: Human Herpesvirus 4

<400> SEQUENCE: 1

Met Gly Ser Leu Glu Met Val Pro Met Gly Ala Gly Pro Pro Ser Pro
 1               5                  10                  15

Gly Gly Asp Pro Asp Gly Tyr Asp Gly Gly Asn Asn Ser Gln Tyr Pro
```

```
                20                  25                  30
Ser Ala Ser Gly Ser Ser Gly Asn Thr Pro Thr Pro Asn Asp Glu
        35                  40                  45

Glu Arg Glu Ser Asn Glu Glu Pro Pro Pro Tyr Glu Asp Pro Tyr
    50                  55                  60

Trp Gly Asn Gly Asp Arg His Ser Asp Tyr Gln Pro Leu Gly Thr Gln
65                  70                  75                  80

Asp Gln Ser Leu Tyr Leu Gly Leu Gln His Asp Gly Asn Asp Gly Leu
                85                  90                  95

Pro Pro Pro Tyr Ser Pro Arg Asp Asp Ser Ser Gln His Ile Tyr
            100                 105                 110

Glu Glu Ala Gly Arg Gly Ser Met Asn Pro Val Cys Leu Pro Val Ile
                115                 120                 125

Val Ala Pro Tyr Leu Phe Trp Leu Ala Ala Ile Ala Ala Ser Cys Phe
            130                 135                 140

Thr Ala Ser Val Ser Thr Val Val Thr Ala Thr Gly Leu Ala Leu Ser
145                 150                 155                 160

Leu Leu Leu Leu Ala Ala Val Ala Ser Ser Tyr Ala Ala Ala Gln Arg
                165                 170                 175

Lys Leu Leu Thr Pro Val Thr Val Leu Thr Ala Val Val Thr Phe Phe
                180                 185                 190

Ala Ile Cys Leu Thr Trp Arg Ile Glu Asp Pro Pro Phe Asn Ser Leu
            195                 200                 205

Leu Phe Ala Leu Leu Ala Ala Ala Gly Gly Leu Gln Gly Ile Tyr Val
            210                 215                 220

Leu Val Met Leu Val Leu Leu Ile Leu Ala Tyr Arg Arg Arg Trp Arg
225                 230                 235                 240

Arg Leu Thr Val Cys Gly Gly Ile Met Phe Leu Ala Cys Val Leu Val
                    245                 250                 255

Leu Ile Val Asp Ala Val Leu Gln Leu Ser Pro Leu Leu Gly Ala Val
                260                 265                 270

Thr Val Val Ser Met Thr Leu Leu Leu Ala Phe Val Leu Trp Leu
                275                 280                 285

Ser Ser Pro Gly Gly Leu Gly Thr Leu Gly Ala Ala Leu Leu Thr Leu
    290                 295                 300

Ala Ala Ala Leu Ala Leu Leu Ala Ser Leu Ile Leu Gly Thr Leu Asn
305                 310                 315                 320

Leu Thr Thr Met Phe Leu Leu Met Leu Leu Trp Thr Leu Val Val Leu
                325                 330                 335

Leu Ile Cys Ser Ser Cys Ser Ser Cys Pro Leu Ser Lys Ile Leu Leu
                340                 345                 350

Ala Arg Leu Phe Leu Tyr Ala Leu Ala Leu Leu Leu Ala Ser Ala
            355                 360                 365

Leu Ile Ala Gly Gly Ser Ile Leu Gln Thr Asn Phe Lys Ser Leu Ser
            370                 375                 380

Ser Thr Glu Phe Ile Pro Asn Leu Phe Cys Met Leu Leu Leu Ile Val
385                 390                 395                 400

Ala Gly Ile Leu Phe Ile Leu Ala Ile Leu Thr Glu Trp Gly Ser Gly
                405                 410                 415

Asn Arg Thr Tyr Gly Pro Val Phe Met Cys Leu Gly Gly Leu Leu Thr
            420                 425                 430

Met Val Ala Gly Ala Val Trp Leu Thr Val Met Ser Asn Thr Leu Leu
                435                 440                 445
```

```
Ser Ala Trp Ile Leu Thr Ala Gly Phe Leu Ile Phe Leu Ile Gly Phe
    450                 455                 460

Ala Leu Phe Gly Val Ile Arg Cys Cys Arg Tyr Cys Cys Tyr Tyr Cys
465                 470                 475                 480

Leu Thr Leu Glu Ser Glu Glu Arg Pro Pro Thr Pro Tyr Arg Asn Thr
                485                 490                 495

Val

<210> SEQ ID NO 2
<211> LENGTH: 7
<212> TYPE: PRT
<213> ORGANISM: Homo sapiens

<400> SEQUENCE: 2

Pro pro Pro gly Arg Arg Pro
1               5

<210> SEQ ID NO 3
<211> LENGTH: 8
<212> TYPE: PRT
<213> ORGANISM: Human Herpesvirus 4

<400> SEQUENCE: 3

Pro Pro Pro Gly Met Arg Pro Pro
1               5
```

ASSAYS AND THERAPIES FOR LATENT VIRAL INFECTION

This application is a divisional application of U.S. patent application Ser. No. 10/646,132, filed on Aug. 22, 2003, now U.S. Pat. No. 7,078,173, at the time of filing of the current application, which is a divisional application of U.S. patent application Ser. No. 09/718,693, filed Nov. 22, 2000, now U.S. Pat. No. 6,642,008, which claims priority to U.S. Provisional Patent Application No. 60/167,212, filed Nov. 24, 1999. The entire text of the above-referenced applications are specifically incorporated herein by reference without disclaimer.

BACKGROUND OF THE INVENTION

This is in the area of the prevention, diagnosis, and treatment of latent viral infections, such as infections with DNA viruses like Epstein-Barr virus.

Epstein-Barr virus has been known for more than three decades. Epstein-Barr has been associated with cancer and several autoimmune diseases. Since there is evidence implicating Epstein-Barr virus in infectious mononucleosis, B cell lymphoma (in immunocompromised hosts), Burkitt's lymphoma, nasopharyngeal carcinoma, and some cases of Hodgkin's lymphoma, there have been efforts to provide a vaccine against Epstein-Barr virus (Morgan, A. J., et al. *J. Med. Virol.* 29:74-78 (1989); Morgan, A. *J. Vaccine* 10:563-571 (1992); Morgan, A. J. *Development of Epstein-Barr Virus Vaccines* (R. G. Landes Company, Austin, Tex. (1995 by Springer-Verlag, Heidleberg, Germany)); Krause, P. R. & Strauss, S. E. *Infect. Dis. Clin. N. A.* 13:61-81 (1999)). Recombinant vectors expressing gp340/220 in a bovine papillomavirus vector or in an adenovirus vector protected five of six cottontop tamarins from lymphomas that otherwise occur after infection with Epstein-Barr virus (Finerty, S., et al. *J. Gen. Virol.* 73:449-453 (1992)). A subunit of the gp340/200 in alum only protected three of five cotton top tamarins from lymphomas (Finerty, S., et al. *Vaccine* 12:1180-1184 (1994)), suggesting that this strategy might not be especially effective. A trial of an Epstein-Barr virus vaccine of gp340/220 in a Vaccinia virus vector has been reported from China and failed to protect a third of those immunized from infection (Gu, S. et al. *Dev. Biol. Stand.* 84:171-177 (1995)), consistent with the primate data. Khanna, et al., *J. Immunol.* 162:3063-3069 (1999) reports on the potential use of gp350/gp85 CTL epitopes in vaccine design to protect against EBV. However, as they note, evidence of neutralizing antibodies does not always correlate with protection against infection. Their research is focused on structural antigens, gp350 and gp85, from which they synthesized specific peptides to use as vaccines. They observed higher CTL reactivity to lytic antigens as compared to a latent antigen, LMP-1. Jackman, et al., *Vaccine* 17:660-668 (1999) also reported on studies using gp350. Gu, et al., *Dev. Biol. Stand.* 84:171-177 (1995) reports on a clinical trial based on live recombinant vaccinia virus expression gp350 as an immunogen, but there were safety concerns.

Another method of vaccine development has been considered. Cytotoxic T cell epitopes have been mapped for several different EBV antigens in persons of specific HLA haplotypes. For example, trials are underway to evaluate the usefulness of immunization with an EBNA-3 peptide which is a dominant CTL epitope in HLA-B8 restricted persons (Schmidt, et al. *Proc. Natl. Acad. Sci. USA* 88:9478-82 (1991)). Efficacy of these vaccines is currently unknown.

A variety of additional therapies against Epstein-Barr virus have been attempted. These include inducing the lytic cycle in cells latently infected by virus (Gutierrez, M. I., et al. *Cancer Res.* 56:969-972 (1996)). Patients with the Epstein-Barr virus related lymphomatoid granulomatosis have been treated with interferon-alpha 2b (Wilson, W. H., et al. *Blood* 87:4531-4537 (1996)). Cycloheximide and acycloguanosine have been demonstrated to be useful in vitro (Ishii, H. H., et al. *Immunol. Cell Biol.* 73:463-468 (1995)); however, only limited further evaluation of this therapy has proceeded due to the limited clinical benefit of acycloguanosine in primary EBV infection.

Therapy with a T cell line has been attempted (Kimura, H. et al. *Clin. Exp. Immunol.* 103:192-298 (1996)), as has adoptive transfer of gene-modified virus-specific T lymphocytes (Heslop, H. E. et al. *Nature Med.* 2:551-555 (1996)). Data available do not appear to particularly support the use of acyclovir for Epstein-Barr virus infections (Wagstaff, A. J., et al. *Drugs* 47:153-205 (1994)), though FK506 (a relative of cyclosporine) may have some benefit (Singli, N., et al. *Digestive Dis. Sci.* 39:15-18 (1994)). Monoclonal antibodies have been used to treat the virus-induced lymphoproliferative syndrome (Lazarovots, A. l., et al. *Clin. Invest. Med.* 17:621-625 (1994)) with modest early success.

Therapeutic strategies directed against the latent phase of the viral infection have been considered. Among these is the consideration of the use of T cell epitopes of particular HLA-restricted cytotoxic T cells (e.g. see Morgan, A. J. *Development of Epstein-Barr Virus Vaccines* (R. G. Landes Company, Austin, Texas (1995 by Springer-Verlag, Heidleberg, Germany), pp 109-115; or Bames J. *Pharma Weekly* 1:11 (1995)). The latent membrane proteins have not been shown to be accessible on the outside of the cell.

Epstein-Barr virus is most similar to the other members of the Herpesviridae family. Although only gamma herpesvirus which infects humans, all human herpesviruses have linear double-stranded DNA, an icosadeltahedral capsid, a tegument which surrounds the capsid and an envelope containing viral glycoprotein spikes on its surface. All human herpesviruses remain with and survive in the host after primary infection.

Cytomegalovirus, in a manner similar to Epstein-Barr virus, is able to establish latency in peripheral immune cells; however, the exact cellular location is still in dispute (Mocarski, E. S. "Cytomegaloviruses and their replication" *Fields Virology*, third edition (eds. B. N. Fields, et al., Lippincott-Raven (1996)), 2447-2480). Human CMV has been treated with a host of antiviral agents, including leukocyte interferon, interferon stimulators, transfer factor, acyclovir and nucleoside inhibitors, as well as combination therapy with interferon and ara-A (reviewed by Alford, C. A. *Antiviral agents and viral diseases of man* $2^{nd}$ ed. New York: Raven Press; 433-86 (1984); Ho, M. *Cytomegalovirus. biology and infection: current topics in infectious disease* New York: Plenum Press; 105-18 (1982)). Very little to no clinical benefit has been demonstrated with these therapies and overwhelming toxicities are present (Alford, C. A. *Antiviral agents and viral diseases of man* $2^{nd}$ ed. New York: Raven Press; 433-86 (1984)).

Gancyclovir (through its nucleic acid chain-terminating activity) and foscarnet (through inhibition of viral DNA polymerase directly) have both been used with success (Snoeck, R., Neyts, J., De Clerq, E. *Multidisciplinary approach to understanding cytomegalovinis disease* Amsterdam: Excerpta Medica: 1993, 269-78). Both of these drugs have been used with some success in the prophylaxis of invasive CMV in the post-transplant setting. However, drug toxicity and no evident decrease in overall mortality limits their standard use for all patients (Goodrich, J. M, et al. *Ann. Intern. Med.* 118:173-8 (1993); Reusser P, et al. *J. Infect. Dis.* 166: 473-79 (1992)).

Passive immunoprophylaxis remains very controversial. Newer drugs targeting the CMV protease and DNA processivity activity are under development (Digard, P., Chow, C. S., Pirrit, L., Coen, D. M. *J. Virol.* 67:1159-68 (1993); Ertl, P. F., Powell, K. L. *J. Virol.* 66:4126-33 (1992)).

Vaccine development for CMV has met with only limited success. Initial studies were performed using an attenuated laboratory strain of CMV (Elek, S. D., Stern, H. Lancet 1:1-5 (1974); Plotkin, S. A., et al. *Infect. Immun.* 12:521-27 (1975)). These British studies showed limited immunity which decreased with time (Plotkin, S. A., et al. *J. Infect. Dis.* 159:860-65 (1989)). Safety issues concerning immunization of slightly immunocompromized subjects and women of childbearing age have also limited excitement over these studies. Subunit vaccines for CMV prevention are also under consideration. Early studies with the major envelope glycoprotein, gB, are under way (Plotkin, S. A., et al. *Rev. Infect. Dis.* 12:827-38 (1990); Spaete, R. R., *Transplant Proc.* 23:90-96 (1991)) and show some early promise.

Human alphaherpesviruses, including herpes simplix-1, herpes simplex-2, varicella-zoster and human herpesvirus 8, primarily establish latency in the sensory ganglia. Substantial evidence is present for the chemotherapy of the herpes-simplex viruses with specific anti-viral therapy, such as acyclovir, gancyclovir and forcarnet (reviewed Rickinson, A. B., Kieff E., "Epstein-Barr virus", *Fields Virology* 2397-2446 (1996)). Numerous vaccines for HSV-1 and HSV-2 have been developed with poor success (reviewed by Whitley, R. J. "Herpes Simplex viruses", *Field's Virology* 2297-2330 (1996)). Two new approaches are of interest. One is based upon the production of adequate amounts of recombinant HSV-2 glycoproteins B or D to be used either separately or together as a subunit vaccine (Ashley, R., Mertz, G. J., Corey, L. *J. Virol.* 61:253-8 (1987); Zarling, J. M., et al. *J. Virol.* 62:4481-85 (1988)). Concerns with these studies include the use of Freund's adjuvant or a lipophilic muramyl tripeptide, neither of which is acceptable human adjuvants. The second method is to genetically engineer a live, attenuated recombinant HSV that combines type 1 and type 2 genomes without the putative neurovirulence sequences (Meignier, B., Longnecker, R., Roizman, B. *J. Infect. Dis.* 162:313-21 (1990)).

*Varicella zoster* also establishes latency in sensory neurons. This virus in its typical primary infection of the juvenile host is only treated with supportive measures with full recovery usually within one week. However, life-threatening primary and recurrent infections are encountered in immunocompromized hosts. These overwhelming infections are usually treated with acyclovir. Gancyclovir and famcylovir are used for treatment of resistant strains. A live, attenuated varicella vaccine is in common use; however, long-term efficacy studies for this vaccine are still pending.

The human herpesvirus-8 is the other alpha herpesvirus. Only recently identified and characterized, neither therapy trials nor vaccine development has yet begun.

The problem within latent viral infections is the ability to identify, target, and treat cells harboring latent virus. For example, the Epstein-Barr virus produces certain proteins during the latent stage of its life cycle. These proteins have not been shown to be antigenic in an expression system that would enable immune system recognition. One of these proteins is LMP-2A. Antibodies have been raised against LPM-2A and immunofluoresence used to show that LMP-2A is located in or near the membrane (Longnecker, R. and Kieff E., *J. Virol.* 64:3219-2326 (1990)). These workers established that their antiserum bound to LMP-2A isolated from the cell, but it was not established that the extracellular part of LMP-2A was antigenic, i.e., could elicit antibody production or was accessible to be bound by antibody (or any other external ligand). In fact, these workers concluded that their antibodies recognized the intracellular portion of LMP-2A because the antibodies were LMP-2A specific and it is the LMP-2A intracellular region which differentiates LMP-2A from LMP-2B. (Actually, these two Epstein-Barr virus proteins are in large part identical and appear to vary because splice junction variation gives LMP-2A a longer amino terminal cytoplasmic tail than is found in LMP-2B.)

It is therefore an object of the present invention to provide methods to target cells that are infected with a virus, such as a DNA virus like a herpes virus, in the latent stage of its life cycle.

It is a further object of the present invention to provide strategies to target cells containing Epstein-Barr virus in a latent state.

It is another object of the present invention to provide strategies to treat or prevent diseases linked to these latent viruses.

It is another object of the present invention to provide vaccines based upon the structure of proteins expressed during the latent life cycle of a virus, such as Epstein-Barr virus.

It is a further object of the present invention to provide methods for the development of therapeutics to treat diseases linked to Epstein-Barr virus by targeting cells latently infected with Epstein-Barr virus.

It is a further object of this invention to provide diagnostics which will identify people with latent viral infections, such as infections with Epstein-Barr virus.

It is a further object of this invention to provide diagnostic tests which will help distinguish those with a disease from those without a disease by differences in the immune responses to a DNA virus, such as Epstein-Barr virus.

SUMMARY OF THE INVENTION

Compositions that bind viral proteins that are specifically expressed during the latent stage of the viral life cycle are disclosed. These compositions bind the latent viral proteins while the viral proteins are expressed in their cellular host, and provide a means for targeting cells that harbor latent virus. In a preferred embodiment the compositions are antibodies which bind the extracellular region of the latent viral protein, most preferably LMP-2A, an EBV latent protein, which are conjugated to a diagnostic or cytotoxic agent or immobilized to a solid support for removal of the infected cells. These antibodies are capable of distinguishing cells expressing EBV DNA from cells which are not expressing EBV DNA. Compositions that can be used to elicit production of these antibodies, or as a vaccine, are also disclosed.

Methods for generating diagnostic or cytotoxic reagents and vaccines based on the viral epitopes that identify cells harboring latent virus are also disclosed.

The antibody conjugates can be used in diagnostic assays to identify cells expressing latent viral protein and people who are harboring latent viral particles. The antibody conjugates can also be used to remove the infected cells or to kill the infected the cells. Alternatively, or in addition, the viral proteins or portions thereof can be used as a vaccine to induce an immune reaction by the host to kill the infected cells. These methods can be used to detect or treat patients harboring latent viruses like EBV and who are at risk of developing a disease such as an autoimmune disease-like systemic lupus erythematosus (SLE) and-rheumatoid arthritis (RA).

DETAILED DESCRIPTION OF THE INVENTION

Definitions

As used herein, autoimmune diseases are diseases that are primarily autoimmune, as well as diseases which do not appear to be primarily autoimmune but have immune manifestations involving immunoglobulins, antigen specific B cell surface receptors (surface immunoglobulins), or antigen-specific T cell receptors. Examples of diseases which fall into these categories are systemic lupus erythematosus, Sjogren's syndrome, rheumatoid arthritis, juvenile onset diabetes mellitus, Wegener's granulomatosis, inflammatory bowel disease, polymyositis, dermatomyositis, multiple endocrine failure, Schmidt's syndrome, autoimmune uveitis, Addison's disease, adrenalitis, primary biliary cirrhosis, Graves' disease, thyroiditis, Hashimoto's thyroiditis, autoimmune thyroid disease, pernicious anemia, gastric atrophy, chronic hepatitis, lupoid hepatitis, atherosclerosis, presenile dementia, demyelating diseases, multiple sclerosis, subacute cutaneous lupus erythematosus, hypoparathyroidism, Dressler's syndrome, myasthenia gravis, autoimmune thrombocytopenia, idiopathic thrombocytopenic purpura, hemolytic anemia, autoimmune hemolytic anemia, pemphigus vulgaris, pemphigus, bullous pemphigoid, dermatitis herpetiformis, alopecia areata, autoimmune cystitis, pemphigoid, scleroderma, progressive systemic sclerosis, CREST syndrome (calcinosis, Raynaud's esophageal dysmotility, sclerodactyly, and telangiectasia), adult onset diabetes mellitus (Type II diabetes), male or female autoimmune infertility, ankylosing spondylitis, ulcerative colitis, Crohn's disease, mixed connective tissue disease, polyarteritis nodosa, systemic necrotizing vasculitis, juvenile onset rheumatoid arthritis, glomerulonephritis, atopic dermatitis, atopic rhinitis, Goodpasture's syndrome, Chagas' disease, sarcoidosis, rheumatic fever, asthma, recurrent abortion, anti-phospholipid syndrome, farmer's lung, erythema multiforme, postcardotomy syndrome, Cushing's syndrome, autoimmune chronic active hepatitis, bird-fancier's lung, asthma, allergic disease, allergic encephalomyelitis, toxic necrodermal lysis, alopecia, Alport's syndrome, alveolitis, allergic alveolitis, fibrosing alveolitis, interstitial lung disease, erythema nodosum, pyoderma gangrenosum, transfusion reaction, leprosy, malaria, leishmaniasis, trypanosomiasis, chronic fatigue syndrome, fibromyalgia, Takayasu's arteritis, Kawasaki's disease, polymyalgia rheumatica, temporal arteritis, schistosomiasis, giant cell arteritis, ascariasis, aspergillosis, Sampter's syndrome (triaditis also called, nasal polyps, eosinophilia, and asthma), Behcet's disease, Caplan's syndrome, dengue, encephalomyositis, endocarditis, myocarditis, endomyocardial fibrosis, endophthalmitis, erythema elevatum et diutinum, psoriasis, erythroblastosis fetalis, fascitis with eosinophilia, Shulman's syndrome, Felty's syndrome, filariasis, cyclitis, chronic cyclitis, heterochromic cyclitis, Fuch's cyclitis, IgA nephropathy, Henoch-Schonlein purpura, glomerulonephritis, graft versus host disease, transplantation rejection, cardiomyopathy, Alzheimer's disease, parvovirus infection, rubella virus infection, post vaccination syndromes, congenital rubella infection, Hodgkin's and non-Hodgkin's lymphoma, renal cell carcinoma, multiple myeloma, Eaton-Lambert syndrome, relapsing polychondritis, malignant melanoma, cryoglobulinemia, hepatitis B virus infection, hepatitis C virus infection, Waldenstrom's macroglobulinemia, mumps virus infection, thrombotic throbocytopenic purpura and any other disorder in which the specific recognition of the host by immunoglobulin, B cell surface receptor (surface immunoglobulin), or T cell receptor is suspected or shown to be important in any aspect of the pathogenesis of the clinical illness.

Immunodeficiency is any reduction in humoral and/or cellular immunity of the normal young adult level which decreases the capacity to protect from infection or respond to an immunogen. Examples of immunodeficiency include infections (tuberculosis, human immunodeficiency virus (HIV) infection, malaria, parasitic infections and a host of others), extremes of age (the fetus, neonates, young children (less than 2 years of age), and old age (over 65 years of age), trauma, severe anemia, burns, exposure, nutritional deficiencies (nutritional, vitamin, starvation, etc.), cancers, hereditary, acquired immunodeficiences due to medications (i.e. transplantation patients, chemotherapy patients, etc.), immune deficiencies (of immunoglobulin, T cells, any number of other genetic defects, etc.) and idiopathic diseases with acquired immune deficiency (sarcoidosis, rheumatoid arthritis, systemic lupus erythematosus, etc.).

Immunization is any procedure which leads to a cellular or humoral immune response directed against an identifiable and specific antigen, usually the immunogen. An antigen is a substance that is bound by antibody or leads to a T cell mediated immune response.

An autoantigen is a constituent of self that binds antibody (making it an autoantibody) or that induces a cellular response, for example, by a T cell. The cellular response may be assayed by presentation of a peptide from the autoantigen, proliferation, cell activation, the prevention of cell activation, secretion of cytokines, activation of apoptosis, or other indication of an effect of the presence of the autoantigen.

An autoantibody is any immunoglobulin, antigen specific B cell surface receptor (surface immunoglobulin), or antigen specific T cell receptor directed against self-protein, carbohydrate or nucleic acid. Such T cell receptors usually bind peptides which themselves are bound by histocompatability molecules. The T cell receptor usually binds to both the peptide and the histocompatibility molecule.

Therapy is a treatment by medical or physical means. A "treatment" is the composition used for treating a condition. Antiviral therapy is the use of a treatment in an effort to suppress or eliminate a virus, for example, suppression, elimination or other amelioration of the effect of Epstein-Barr virus.

Peptides are small proteins composed of amino acids, typically at least four to seven amino acids in length, covalently bound to one another by peptide bonds. Peptides may be prepared by an in vivo mechanism, as in life, by using the nucleic acid encoding for the sequence of the peptide produced, or in vitro using peptide chemistry. A vaccine is a composition including antigen that elicits an immune response effective to prevent or ameliorate a disease.

Seroconversion means that the subject has developed antibodies to an immunogen. Usually, this is the result of immunization (vaccination) or infection. Seropositive means that there are a sufficient quantity of antibodies with sufficient affinity to conclude that seroconversion has occurred. Seronegative means that the quantity and affinity of antibodies are not sufficient to conclude that seroconversion has occurred. In this application, the terms "lupus" and "systemic lupus erythematosus" are used interchangeably.

The term linear epitope as defined by a specific sequence is used herein to include peptides having substitutions yielding a peptide bound in an equivalent manner or extent by an antibody or autoantibody.

I. Compositions for Diagnosis and Treatment of Latent Infections

Compositions have been prepared based on information regarding unique epitopes of molecules specific to latently infected cells. This is exemplified in the attached examples. In general, viral proteins, expressed only on the surface of latently infected cells, are identified and antibodies prepared which are reactive with the extracellular portion of the proteins. These antibodies may be prepared using isolated antigen, followed by screening for reactivity with latently infected cells, or by immunization with an extracellular fragment (prepared by enzymatic cleavage or recombinant techniques), alone or in combination with an adjuvant or as a fuision protein. The antibodies can be used as whole antibodies, antibody fragments, labeled with diagnostic labels, or bound to a cytotoxic agent to kill infected cells. Alternatively, the antigens can be used to prepare vaccines which are used to immunize an individual who has, or is at risk of, a latent viral infection.

Viruses

There are a number of different classes of viruses. There are class I and class II DNA viruses, differentiated by the fact that class I viruses contain nucleic acid in a double-stranded genome and class II viruses contain nucleic acid in a single-stranded genome. Adenoviruses, Herpesviruses, SV40 viruses, and Vaccinia viruses are all class I and Parvoviruses are class II viruses. Classes III (reovirus), IV (poliovirus), V (vesicular stomatitis virus), and VI (retroviruses) are RNA viruses.

Some viruses have two stages: (1) when the virus is infectious, the lytic stage, and (2) when the virus can persist in the host, the latent stage.

The lytic stage produces new viral particles, which are infectious. During the lytic stage the viral gene products expressed are sufficient to commandeer the cellular machinery to make new viral particles. When a virus is in a lytic stage, the amount of viral material ensures that nearly all infected individuals will develop an immune response to at least some part of the virus. Consequently, a vigorous immune response against the virus and the virus producing host cells usually develops when the virus is in the lytic stage.

During the latent stage the virus expresses only a few of its gene products and its genetic material is passed to daughter cells during cell division. Since only small amounts of very few proteins are expressed from the viral genome, and since there are specific mechanisms in latency to avoid immune recognition or to inhibit anti-viral immunity, the immune response to viral material which is produced during some the latent stages of the life cycle is small or non-existent. Consequently, the virus can survive in the infected host for many years. The host most often remains infected for the duration of its life.

Infrequently, a latent virus can become "activated" and the infections become lytic. New virus is then made and the infection is spread in the host, unless the immune response of the host intervenes to prevent the successful production of new virus. This process typically occurs and reoccurs throughout the life of the host.

Epstein-Barr Virus

Epstein-Barr virus is a herpes virus, Human Herpes Virus 4 (HHV-4). This virus is from the genus *Lymphocryptovirus* and subfamily gammaherpesvirinae. This is the only gamma herpes virus known in man. Like the other herpes viruses, this is a DNA virus and has a strong propensity for latency. Once latent this virus emerges from latency at a low level throughout life.

Epstein-Barr virus infects B cells and induces a large number of different antibodies in the early stage of infection. In most people the B cell proliferation and antibody production is eventually brought under control by virus specific T cells. Thereafter, the virus remains latent, surviving in the host for the remainder of the natural life. The virus continues to "reactivate" at a low level, as evidenced by the shedding of virus in the oral cavity, infection through exchange of oral secretions, the spontaneous in vitro outgrowth of transformed B cells, and the spontaneous production of Epstein-Barr virus in vitro. The continuous presence of virus presents a significant challenge to the immune system and requires that the immune mechanisms sustain viral suppression over the many decades of remaining life. The immune system recognizes the antigens of the lytic stage (and whole virus) much better than the latent stage. Most of the T cell responses are directed against lytic stage antigens and may tend to concentrate on the antigen known as EBNA-3A (Epstein-Barr nuclear antigen-3A). CD8 T cell responses against the latent stage antigen ENBA-1 are specifically inhibited, even though antibody is frequently made against this antigen. This effect appears to be caused by inhibition in antigen presentation (Levitskaya J., et al. *Nature* 375:685-88 (1995)).

Three different types of latency have been identified in what are now classic studies: Type 1, Type 2, and Type 3. About eight EBV gene products are known to be expressed in different stages of latency. In Type 1 latency, only EBNA-1 is expressed. In Type 2 latency, LMP-1, LMP-2A and LMP-2B are expressed. These three plus LP, EBNA-1, EBNA-2, EBNA-3A, -3B, and -3C are expressed in Type 3 latency. EBER RNAs may also be expressed in latency. These three forms of latency generally conform to what has been found in Burkitt's lymphoma (in vivo and in cell lines), some lymphomas, nasopharyngeal carcinoma, and transformed B cell lines derived in vitro from normal donors.

Another latent stage has recently been described in which only a single gene, latent membrane protein 2A (or LMP-2A), is expressed (Miyashita, E. *J. Virol.* 71:4882-91 (1997)). The amino acid sequence and DNA sequence of Epstein-Barr virus LMP-2A is found at Swiss Protein DataBank accession number P13285 and GenBank accession number M24212. This form may dominate in normal individuals. A form of latency observed in immunosuppressed patients appears to consist of only EBV DNA with no LMP-2A nor EBNA-1 expression (Babcock G, et al. *J. Exp. Med.*, 190; 567-576 (1999)).

It has been asserted by some that only B lymphocytes are able to generate productive infectious virus (Thorley-Lawson, D. A., Miyashita, E. M., Khan, G., *Trends Micro.* 4:204-8 (1996)). Indeed, some argue that only B cells are infected in the latent state (Mikashita, E. M., et al., *J. Virol.* 71:4882-4891 (1997)). Recent observations by Thorley-Lawson show that multiple forms of latency co-exist in different cells in the same human subject (Babcock G, et al. *J. Exp. Med.*, 190; 567-576 (1999)).

There are also data showing evidence for the expression of Epstein-Barr virus genes in rheumatoid synovium (Scotet E., et al. *J. Exp. Med.* 184:1771-80 (1996)) and in the synovial cells or fibroblasts from these patients (Koide J., et al. *J. Virol.* 71:2478-81 (1997); Takei M., et al., *Int. Immunol.* 9:739-43 (1997)).

It is believed that rheumatoid arthritis may be caused by a dysregulated form of Epstein-Barr virus infection in the synovium. This may involve more genes than just the known latent genes (EBERs, EBNAs, BART, LP, LMPs). While no one has established whether that intact virus is produced, it is thought that the infection is less efficient relative to a normal infection in B cells. This is referred to as an "abortive" or "partial" or "incomplete" EBV infection. The genes expressed include, among others, BZLF1, BMLF1, BCRF1, BMRF1, BALF4, EBNA3A, EBNA3B, EBNA3C, and LMP2. (Scotet et al *Eur J. Immunol.* 29:973-85 (1999)). The T cell immune response in RA synovium appears to be strongest against a few genes involved in signaling the virus to switch from latency to lytic infection.

Other Latent Viruses

Latency in herpes simplex virus-1 and herpes simplex virus-2 is maintained with the latency associated transcripts (LAT). The major open reading frame contains 2 kb of viral DNA. Though CD8+ T cells appear to be important in maintaining latency, the antigen and their relation to LAT is not known. Indeed, the protein products from the LAT genes have never been isolated. An immune response directed against LAT RNA or LAT encoded protein is not known.

In varicella zoster virus, the latently expressed proteins include IE4, IE62, IE63 and ORF29p. IE63 is abundant and antigenic (Straus, S. E., et al. *Ann. Int. Med.* 108:221 (1988); Donahue, J. G. et al. *Arch. Int. Med.* 155:1605-9 (1995); Debras, S. et al. *J. Virol.* 69:3240 (1995); Mahalingham, R., et al. *Proc. Nat'l. Acad. Sci. U.S.A.* 93:2122 (1996); Sadzot-Delvaux, C., et al. *J. Immunol.* 159:2802 (1997); Sadzot-Delvaux, C. & Bentier, B., 24$^{th}$ *International Herpesvinis Workshop* July 17-23 23 (Mass. Inst. Tech.) abst. 9.009 (1999)).

There is much less now known about the latent state of infection with cytomegalovirus than with Epstein-Barr virus. Nevertheless, in both man and mouse a number of genes are expressed in latent cytomegalovirus infection including ORF42, ORF45, ORF55, ORF59, ORF94, 0RF152, and ORF154. Of these, at least ORF152 has a predicted transmembrane domain and may be a membrane protein, and hence have a potential to be a target for therapeutics in a way similar to LMP-2A, as described herein. Cytomegalovirus is a β herpesvirus, as are HHV-6 and HHV-7. It is thought that HHV-6 ORF160 and HHV-7 ORF97 are the latent homologues of HCMV ORF152 (Kondo, K. & Yamanishi, K. 24$^{th}$ *International Herpesvirus Workshop*, July 17-23 (Mass. Inst. Tech.) Abst. 1.016 (1999)). ORF152 has been shown to be antigenic (Kondo, K. et al *Proc. Natl. Acad. Sci. USA* 93;1 1137-42 (1996)), but not whether the antibodies to ORF 152 will bind the surface of cells latently infected with cytomegalovirus.

Kaposi's sarcoma herpesvirus or HHV-8, another oncogenic human gamma herpesvirus, expresses a latent protein called latency associated nuclear antigen ("LANA" or ORF73). LANA has been shown to attach cellular DNA to the episome of Kaposi's sarcoma herpes virus. In addition, ORF71 and ORF72 are expressed in the latent form of HHV-8 (Dittmer D, et al. *J. Virol.* 72:8309 (1998)). Both the Kaposi's sarcoma-associated herpesvirus (Human herpesvirus 8) and *Herpesvirus papio* produce latent membrane proteins similar to EBV LMP-2A (Genbank accession # AAD45297 and accession #AAC54552 respectively). In addition the *Herpesvirus papio* also contains a latent membrane protein similar to EBV LMP-1 (GenBank accession #AAB37764).

Diagnostic and Cytotoxic Agents

The antibodies or fragments thereof can be used to identify, remove and/or kill latently infected cells. Typically, the antibody will be coupled to a label which is detectable or cytotoxic but which does not interfere with binding to the infected cells. Examples include radioisotopes, such as indium ("In"), which is useful for diagnostic purposes, and yttrium ("Y"), which is cytotoxic. Other detectable labels include enzymes, radioisotopes, fluorescent compounds, chemiluminescent compounds, and bioluminescent compounds and compounds detectable by ultrasound, MRI or CT. Other cytotoxic agents include toxins such as ricin, mitomycin C, danorubicin, and vinblastin.

Antibodies to the Latent Viral Proteins

When an antigen is presented to an immune system there are usually many antibodies produced, often recognizing different portions of the antigen. The sera of the antigen challenged animal may contain all or many of these antibodies, referred to as polyclonal antibodies. Each of the antibodies are produced from a single B cell which in turn makes many clonal copies of itself. These B cells can be made into hybridomas which produce a monoclonal antibody.

Antigens have regions called epitopes which make up the specific molecular determinants for antibody:antigen binding. Typically an epitope of a protein is composed of between three or four to eight amino acids (see Watson et al., "Certain Properties Make Substances Antigenic," in *Molecular Biology of the Gene*; Fourth Edition, page 836, paragraph 3, (The Benjamin/Cummings Publishing Company, Menlo Park, 1987)). The antigens that are determinative of the latent stage of a viral infection can contain the entire native epitope, or portions thereof, sufficient to react with antibody.

An antibody to an antigen of choice can be produced in mice according to Kohler and Milstein, *Nature,* 256:495-497 (1975) and *Eur. J. Immunol.* 6:511-519 (1976), both of which are hereby incorporated by reference, by immunizing a host with the antigen of choice. Once a host is immunized with the antigen, B-lymphocytes that recognize the antigen are stimulated to grow and produce antibody to the antigen. Each activated B-cell produces clones which in turn produce the monoclonal antibody. B-cells cannot be cultured indefinitely, however, so hybridomas are produced using the methods developed by Kohler and Milstein, *Nature,* 256:495-497 (1975). The antibodies produced and isolated by this method are specific for a single antigen or epitope on an antigen, and are referred to as monoclonal antibodies.

A cell bound enzyme linked iminmunosorbent assay (ELISA) can be used to screen supernatants from growing hybridomas (Glassy, M. C. and Surh, C. D., *J. Immunol. Method,* 81:115 (1985)). Cells which bind the antibody or produce the antibody can be analyzed using Flow Cytometry. Cell surface antigens are detectable by flow cytometry.

Solid phase binding of antibodies to peptides has proven useful for examining sequential linear epitopes, also referred to as "linear" or "sequential". These have been useful to define important residues in epitope structure. This approach may or may not be less useful in defining conformational epitopes or for defining regions where two or more linear, but not sequential, epitopes are brought together by the tertiary structure. The particular structural relationships between the antigens derived from viral proteins expressed during the latent life cycle of a DNA virus and the antibodies that bind them with particular regard to the specific conformation assumed by the peptide determines what can be learned by this approach. In addition, although many peptides may assume conformations in solution that are not found in the native protein structure, true epitopes may still be delineated by this method. Those peptides that tend to have a structure similar to that found in the native molecule are usually expected to be bound by a larger proportion of the antibodies that bind the analogous sequence on the native protein and/or may be bound with greater affinity.

Useful latent viral proteins to make antibodies for use in the conjugates disclosed herein are described above. Proteins that are expressed on the cell surface of the cells harboring the latent DNA virus are preferred. A preferred latent viral protein is the LMP-2A protein of EBV. Vaccines including this protein, and more preferably the extracellular portion of this protein, and optionally an adjuvant, can be used to immunize patients against the latent infection, or for this application, to make antibodies for use as conjugates. Suitable antibodies can be produced as described in example 1. Though antibodies against the latent membrane proteins have long been appreciated (e.g. Rowe, M. et al., *J. Gen. Virol.* 69:1217-28 (1988)), including a remarkably high frequency of antibodies against LMP-2A and LMP-2B in nasopharyngeal carcinoma (Lennette, E. T. et al., *Eur. J. Cancer* 31A: 1875-8 (1995)), the presence of antibody binding to LMP-2A or LMP-2B from the external cell surface has not been demonstrated previously.

LMP-1 is also expressed during some phases of latency. Depending upon their expression patterns, this membrane protein may also be a useful target for anti-EBV therapeutics in the EBV related diseases, much as LMP-2A appears to be and LMP-2B are.

Other viral proteins of interest include cytomegalovirus (CMV), Kaposi, and other herpes viruses, especially human herpes virus 6, varicella 3, and CMV 5.

While the in vivo use of a monoclonal antibody from a foreign donor species in a different host recipient species is usually uncomplicated, an antigenic site on the donor antibody can cause an adverse immunological response in the organism receiving the donor antibody. The adverse response may serve to hinder the molecular interaction of the donor antibody or acceptance of the donor antibody. Chimeric antibodies can be used to reduce or eliminate the adverse host response (Sun, L. K., et al., *Hybridoma*, 5 (Supplement 1):S17 (1986); Oi, et al., *Bio Techniques*, 4(3): 214 (1986)). Chimeric antibodies are antibodies in which the various domains of the antibodies' heavy and light chains are coded for by DNA from more than one species. Typically, a chimeric antibody will comprise the variable domains of the heavy ($V_H$) and light ($V_L$) chains derived from the donor species producing the antibody of desired antigenic specificity, and the variable domains of the heavy ($C_H$) and light ($C_L$) chains derived from the host recipient species. It is believed that by reducing the exposure of the host immune system to the antigenic determinants of the donor antibody domains, especially those in the $C_H$ region, the possibility of an adverse immunological response occurring in the recipient species will be reduced. Thus, for example, it is possible to produce a chimeric antibody for in vivo clinical use in humans which comprises mouse $V_H$ and $V_L$ domains coded for by DNA isolated from a rabbit that binds LMP-2A and $C_H$ and $C_L$ domains coded for with DNA isolated from a human immune system cell.

Under certain circumstances, monoclonal antibodies of one isotype might be more preferable than those of another in terms of their diagnostic or therapeutic efficacy. For example, from studies on antibody-mediated cytolysis, it is known that unmodified mouse nionoclonal antibodies of isotype gamma-2a and gamma-3 are generally more effective in lysing target cells than are antibodies of the gamma-1 isotype. This differential efficacy is thought to be due to the ability of the gamma-2a and gamma-3 isotypes to more actively participate in the cytolytic destruction of target cells. Particular isotypes of a monoclonal antibody can be prepared either directly, by selecting from the initial fusion, or prepared secondarily, from a parental hybridoma secreting a monoclonal antibody of different isotype by using the sib selection technique to isolate class-switch variants (Steplewski, et al., *Proc. Natl. Acad. Sci., U.S.A.*, 82:8653 (1985); Spira, et al., *J. Immunol. Meth.*, 74:307 (1984)). Thus, the antibodies described herein include class-switch variants having the specificity of monoclonal antibodies derived to the extracellular regions of LMP-2A.

Antibody fragments, such as, for example, Fab and F(ab')$_2$, as well as isotypes, particularly if labeled or bound to a cytotoxic agent, can be used since having an effect on the viral infection in these situations is not dependent upon complement-mediated cytolytic destruction of those cells bearing the latent viral protein.

Those of skill in the art readily understand how to apply the techniques developed for imuunotherapy discussed herein to compositions which do not include an antibody per se, but have the same antigen recognition properties of an antibody. For example, peptides binding an "antigen" which are developed de novo using combinatorial methods can be used to replace the "antibody" in the immunotherapy regimes. These could be coupled to a radioisotope or toxin, for example, for delivery to the target cell, as described below with respect to the antibodies.

Coupling of Diagnostic or Cytotoxic Agents to Antibodies

The diagnostic or cytotoxic agents can be coupled either directly or indirectly to the antibodies. Indirect coupling is typically via a spacer moiety. These spacer moieties, in turn, can be either insoluble or soluble (Diener, et al., *Science*, 231:148 (1986)) and can be selected to enable release of the agent from the antibody molecule at the target site.

Some radioisotopes can be attached directly to the antibody; others require an indirect form of attachment. The radioisotopes $^{125}$I, $^{131}$I, $^{99m}$Tc, $^{186}$Re and $^{188}$Re can be covalently bound to proteins (including antibodies) through amino acid functional groups. For radioactive iodine it is usually through the phenolic group found on tyrosine.

There are numerous methods to accomplish coupling: chloramine-T (Greenwood, et al. *Biochem J.* 89: 114-123 (1963)); and Iodogen (Salacinski, et al. *Anal. Biochem.* 117: 136-146 (1981)). Tc and Re can be covalently bound through the sulfhydryl group of cysteine (Griffiths, et al. *Cancer Res.* 51: 4594-4602 (1991)).

For in vivo diagnosis radioisotopes may be bound to immunoglobin either directly or indirectly by using an intermediate functional group. Intermediate functional groups which often are used to bind radioisotopes which exist as metallic ions to immunoglobins are the bifunctional chelating agents such as diethylenetriaminepentacetic acid (DTPA) and ethylenediaminetetraacetic acid (EDTA) and similar molecules.

The targeting molecule (for example, the antibody), and the agent can be linked in several ways. If the hybrid molecule is produced by expression of a fused gene, a peptide bond serves as the link between the cytotoxin and the antibody or antibody fragment. Alternatively, the toxin and the binding ligand can be produced separately and later coupled by means of a non-peptide covalent bond. For example, the covalent linkage may take the form of a disulfide bond. In this case, the DNA encoding the antibody can be engineered to contain an extra cysteine codon. The cysteine must be positioned so as not to interfere with the binding activity of the molecule. The toxin molecule must be derivatized with a sulfhydryl group reactive with the cysteine of the modified antibody. In the case of a peptide toxin this can be accomplished by inserting a cysteine codon into the DNA sequence encoding the toxin. Alternatively, a sulfhydryl group, either by itself or as part of a cysteine residue, can be introduced using solid phase polypeptide techniques. For example, the introduction of sulfhydryl groups into peptides is described by Hiskey (*Peptides* 3:137 (1981)). The introduction of sulfhydryl groups into proteins is described in Maasen et al. (*Eur. J. Biochem.* 134:32 (1983)). Once the correct sulfhydryl groups are present, the cytotoxin and antibody are purified, both sulfur groups are reduced; cytotoxin and ligand are mixed; (in a ratio of about 1:5 to 1:20) and disulfide bond formation is allowed to proceed to completion (generally 20 to 30 minutes) at room temperature. The mixture is then dialyzed against phosphate buffered saline or chromatographed in a resin such as Sephadex to remove unreacted ligand and toxin molecules.

Numerous types of cytotoxic compounds can be joined to proteins through the use of a reactive group on the cytotoxic compound or through the use of a cross-linking agent. A common reactive group that will form a stable covalent bond in vivo with an amine is isothiocyanate (Means, et al. Chemical modifications of proteins (Holden-Day, San Francisco 1971) pp. 105-110). This group preferentially reacts with the ε-amine group of lysine. Maleimide is a commonly used reactive group to form a stable in vivo covalent bond with the sulfhydryl group on cysteine (Ji, T. H., *Methods Enzymol* 91: 580-609 (1983)). Monoclonal antibodies are incapable of forming covalent bonds with radiometal ions, but they can be attached to the antibody indirectly through the use of chelating agents that are covalently linked to the antibodies. Chelating agents can be attached through amines (Meares, C. F., et al., *Anal. Biochem.* 142:68-78 (1984)) and sulfhydral groups (Koyama, et al., *Chem. Abstr.* 120:217262t (1994)) of amino acid residues and also through carbohydrate groups (Rodwell, J. D., et al., *Proc. Natl. Acad. Sci.* 83:2632-2636 (1986); Quadri, S.M., et al., *Nucl. Med. Biol.* 20:559-570 (1993)). Since these chelating agents contain two types of functional groups, one to bind metal ions and the other to joining the chelate to the antibody, they are commonly referred as bifunctional chelating agents (Sundberg, M. N., et al., *Nature* 250: 587-588 (1974)).

Crosslinking agents have two reactive functional groups and are classified as being homo or heterobifunctional. Examples of homobifunctional crosslinking agents include bismaleimidohexane (BMH) which is reactive with sulfhydryl groups (Chen, L. L., et al. *J Biol Chem* 266: 18237-18243 (1991) and ethylene glycolbis[succinimidylsucciate] EGS which is reactive with amino groups (Browning, J., et al., *J. Immunol.* 143: 1859-1867 (1989)). An example of a heterobifunctional crosslinker is -maleimidobenzoyl-N-hydroxysuccinimide ester (MBS) (Myers, D E et al. *J. Immunol. Meth.* 121(1): 129-142 (1989)). These methodologies are simple and are commonly employed.

Cytotoxic Agents

Toxins and substances which elicit the host to attack the tumor cells, as well as synthetic or natural chemotherapeutic drugs (Halpern, et al., *J. Nucl. Med.* 29:1688-1696 (1988); Quadri, et al., *Nucl. Med. Biol.* 20:559-570 (1993); Wang, et al., *Radiat. Res.* 141:292-302 (1995)), oligonucleotides (Mujoo, et al., *Oncogene* 12:1617-1623 (1996)), cytokines (Markman, *Semin. Oncol.* 18:248-254 (1991); Dedrick, et al., *Cancer. Treat Rep.* 62:1-11 (1978)), and radioactive colloids (Rowlinson, et al., *Cancer Res.* 47:6528-6531 (1987)), can be conjugated to the antibodies using standard chemical techniques, or in some cases, using recombinant. technology, for example, fusion proteins. The antibodies can also be coupled to a signal protein that induces apoptosis (or programmed cell death).

Toxins are poisonous substances produced by plants, animals, or microorganisms that, in sufficient dose, are often lethal. Diphtheria toxin is a substance produced by *Corynebacterium diphtheria* which can be used therapeutically. The toxic alpha component can be bound to the antibody and used for site specific delivery to a cell harboring a latent virus, such as EBV. Diphtheria toxin, whose sequence is known, and hybrid molecules thereof, are described in detail in U.S. Pat. No. 4,675,382 to Murphy.

Lectins are proteins, usually isolated from plant material, which bind to specific sugar moieties. Ricin is a toxic lectin which has been used immunotherapeutically. This is accomplished by binding the alpha-peptide chain of ricin, which is responsible for toxicity, to the antibody molecule to enable site specific delivery of the toxic effect. Other useful toxins include cholera toxin, Shiga-like toxin (SLT-I, SLT-II, SLT-IIV), LT toxin, C3 toxin, Shiga toxin, pertussis toxin, tetanus toxin, *Pseudomonas exotoxin*, alorin, saporin, modeccin, and gelanin. See also Hoch, D. H., et al., *Proc. Natl. Acad. Sci. USA* 82:1692-6 (1985); Colombatti, M., et al., *J. Biol. Chem.* 261:3030-5 (1986); Deleers et al., *FEBS Lett.*, 160:82-6 (1983), Hwang, J., et al. (*Cell* 48:129-36 (1987)); and Gray, G. L., et al. (*Proc. Natl. Acad. Sci. USA* 81:2645-9 (1984)).

Radioisotopes are small and well characterized, and can be used as diagnostics and followed after administration using standard non-invasive radioimaging techniques. Certain radioisotopes may be more preferable than others depending on such factors as viral distribution as well as isotype stability and emission characteristics. In general, alpha and beta particle-emitting radioisotopes are preferred in immunotherapy. Preferred are short range, high energy alpha emitters such as $^{212}$Bi. Examples of radioisotopes which can be bound to the disclosed antibodies for therapeutic purposes are $^{125}$I, $^{131}$I, $^{90}$Y, $^{67}$Cu, $^{212}$Bi, $^{211}$At, $^{212}$Pb, $^{47}$SC, $^{109}$Pd, and $^{188}$Re.

As radioisotopes decay, they emit characteristic photons or particles or both. Photons, commonly referred to as gamma rays, are penetrating. If their energy level is high enough, they can travel through the body and be detected by diagnostic instrumentation. Radioisotopes that emit photons can be attached to an antibody and used for diagnostic imaging. This application is termed radioimmunoscintigraphy (RIS). The shorter the distance between the antigen and the target, the shorter the required range of emission of the radioisotope. Auger electrons have a very short path length (5-10 nm) and need to be internalized to be cytotoxic (Adelstein, et al., *Nucl. Med. Biol.* 14:165-169 (1987)). Only antibodies that are internalized after binding to a cell should be considered for radioisotopes that emit Auger electrons. Alpha particles need to be close to a cell (within 3-4 cell diameters) to be effective (Vriesendorp, et al., Radioimmunoglobulin therapy. In: High Dose Cancer Therapy. Armitage, et al. (eds). (Williams & Wilkins, Baltimore, Md. 1992) pp. 84-123). Both Auger electrons and alpha emitters have high selectivity because their short-range emission will not irradiate neighboring normal cells.

The radiometals $^{111}$In and $^{90}$Y are, respectively, pure γ- and pure β-emitters. Iodine-125, the most commonly used emitter of Auger electrons, has a half-life of 60 days and frequently is released by the immunoconjugate in vivo (dehalogenation) (Vriesendorp, et al., 1992). The most commonly considered alpha emitters for clinical use, astatine-211 and bismuth-212, have short half-lives (7.2 h and 1.0 h, respectively) and decay into radioactive isotopes, that may not be retained by the immnunoconjugate after the first alpha emission (Wilbur, *Antibiot. Immunoconjug. Radiopharm.* 4:85-97 (1991)).

The antibodies can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI.

Vaccines

Vaccines to induce a reaction to the latent viral proteins, will typically consist of the viral protein, most preferably an extracellular portion thereof, as described above, alone or in combination with an adjuvant. Numerous vaccine formulations are known to those skilled in the art.

As discussed above, EBV produces cells expressing LMP-2A, which are latently infected cells. LMP-2A peptides, or the entire protein, can be obtained by isolating the naturally occurring protein, or more preferably, engineered peptides can either be made through synthetic mechanisms or through recombinant biotechnology techniques. Peptides of up to about forty amino acids, more preferably between four and twenty-five amino acids, most preferably between four and eight amino acids, can be synthesized using any one of the methods known to those skilled in the art. Immunogenic fusion protein derivatives can be made by fusing a polypeptide sufficiently large to confer immunogenicity to the target sequence by cross-linking in vitro or by recombinant cell culture transformed with DNA encoding the fusion. For example, chimeric proteins consisting of multiple epitopes from one or more latent viral proteins can be used to generate a more immunogenic molecule for administration as a vaccine.

Peptide molecules can be generated in a variety of ways well known to those of ordinary skill in the art. An example is the solid phase synthesis described by J. Merrifield (*J. Am. Chem. Soc.* 85, 2149 (1964)), used in U.S. Pat. No. 4,792,525, and described in U.S. Pat. No. 4,244,946, wherein a protected alpha-amino acid is coupled to a suitable resin, to initiate synthesis of a peptide starting from the C-terminus of the peptide. Other methods of synthesis are described in U.S. Pat. Nos. 4,305,872 and 4,316,891. These methods can be used to synthesize peptides having identical sequence to the proteins described herein, or substitutions or additions of amino acids, which can be screened for activity as described above.

Recombinant DNA technology can be used to generate large numbers of peptides. Indeed, one approach uses what is called a phage display library. Here the DNA is transcribed into mRNA which is then translated to become part of the minor pili protein. By randomly varying the critical part of the DNA, a large number of peptides are prepared, which can include all of the theoretically possible peptides. In addition to their use in vaccines, the peptides can be used to evaluate antigenicity or other interactions between ligands.

Pharmaceutically Acceptable Carriers

The compositions, including antibodies, can be used therapeutically in combination with a pharmaceutically acceptable carrier.

Pharmaceutical carriers are known to those skilled in the art. These most typically would be standard carriers for administration of vaccines to humans, including solutions such as sterile water, saline, and buffered solutions at physiological pH. Other ingredients include excipients, carriers, thickeners, diluents, buffers, preservatives, and surface active.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, and lactated Ringer's. Preservatives and other additives may also be present such as, for example, antimicrobials, anti-oxidants, chelating agents, and inert gases.

The immunogenic peptides can also be administered in a viral vector, such as an adenoviral vector, which infects cells, presents the latent viral protein epitopes on the surfaces of the infected cells and thereby elicits the immune response against the virus, i.e., EBV. Suitable adenoviral vector and vaccinia virus systems are described by Ranier, et al., *J. Virol.* 73(12): 10416-10425 (1999) and Stewart, et al., *Vaccine* 17:152-157 (1999), respectively. Alternatively, the immunogenic peptides can be administered as DNA in a plasmid, which can be administered directly as naked DNA, in cells, and/or encapsulated in a polymer such as microspheres or hydrogels. These techniques are well known to those skilled in the art. Charo, et al., *J. Immunol.* 163:5913-5919 (1999) describes a suitable plasmid delivery system. Polymeric carriers and other delivery systems are described, for example, in U.S. Pat. Nos. 6,133,026, 6,080,728, 6,048,736, 5,985,573, 5,869,103, and 5,783,567.

Substrates for Removal of Infected Cells

The latently infected cells, once identified by the compositions herein, can be separated from the remainder of the cells following procedures such as bone marrow or solid organ transplants, or by standard techniques such as plasmapheresis. These tend not to be selective, however.

More preferably, infected cells are removed with a selective process. For example, antibody can be covalently bound to a solid phase and employed as a composition for separation of latently infected cells from the remainder of cells. In a preferred embodiment, the patient's blood is passed through an extracorporeal reactor or filter having the anti-viral antibodies immobilized thereon or therein. Typical filters are of the type used for kidney dialysis and can be attached to the patient in the same manner. Conventional coupling techniques, such as those described above, are used to secure the antibodies to the nitrocellulose membranes in the dialyser units.

II. Methods of Diagnosis and Treatment

There are a number of uses for the disclosed compositions, for example, in diagnostic assays and kits, vaccine preparations, and a variety of therapies.

The destruction of cells harboring latent virus should reduce the effects of the virus on the host and moderate or prevent any subsequent diseases that are dependent on the presence of the DNA virus. For example, diseases such as lupus (or any of the other diseases thought to be caused by EBV) which are believed to require the continued presence of the EBV infection in order to maintain the disease process, could thereby be moderated by the reduction in EBV infected cells.

Therapies

Diseases to be Treated

Latent viral infections have been correlated with certain diseases, for example, EBV infection is correlated with autoimmune disease and cancer, as demonstrated by a number of published studies.

For example, a Japanese group found a high frequency of antibodies against Epstein-Barr virus Nuclear Antigens 2 and 3 in lupus patient sera (an autoimmune disease), compared to normal controls (Kitagawa, H., Et al. *Immunol. Lett.* 17:249-252 (1988)). Another Japanese group found higher levels of antibody directed against a membrane antigen from Epstein-Barr virus in lupus (and rheumatoid arthritis) sera than in controls (Yokochi, T. et al. *J. Rheumatol.* 16:1029-1032 (1989)). Similarly, an Australian group found a modest increase in antibodies against early antigens (Sculley, D. G., et al. *J. Gen. Virol.* 67:2253-2258 (1986)). An Italian group has shown that the affinity purified antibodies from the 95-119 region of Sm D from lupus patients bind the Epstein-Barr virus Nuclear Antigen-I between amino acids 35 and 58 (Sabbatini, A., et al. *Eur. J. Immunol.* 23:1146-1152 (1993)). The most recent contribution to this question uses both molecular methods to detect Epstein-Barr DNA and serologic methods to detect antibodies to Epstein-Barr virus (Tsai, Y. et al. *Int. Arch. Allergy Immunol.* 106:235-240 (1995)). These studies show no significant differences between lupus patients and controls.

Morshed and colleagues published data showing an increased level of Epstein-Barr virus DNA in patients with primary biliary cirrhosis compared to controls from peripheral blood mononuclear cells, saliva, and fixed liver tissue (Morshed, S. A. et al. *Gastroenterol. Jpn.* 27:751-758 (1992)). The nuclear dot antigen is an autoantigen bound by autoantibody found in a few sera from patients with primary biliary cirrhosis. This autoantibody is uncommonly found in lupus and rheumatoid arthritis sera. Analysis of the epitopes of the nuclear dot antigen has revealed two epitopes which have homology with Epstein-Barr virus protein sequences (Xie, K. and Snyder, M. *Proc. Natl. Acad. Sci.* 92:1639-1643 (1995)).

Evidence consistent with a relationship between lupus and EBV is the following: The anti-Sm response may develop as a consequence of molecular mimicry between PPPGRRP of EBNA-1 and PPPGMRPP of the Sm B/B' autoantigen of the spliceosome (James J A and Harley J B, *J. Immunol.* 148:2074-79 (1992); James J A, et al. *J. Exp. Med.* 181:453-61 (1995)). EBV infection is associated with lupus in both children and adults (James J A, et al. *J. Clin. Inv.* 100:3019-26; James J A and Harley J B *Arthritis Rheum.*, in press (1999)). The immune response against EBV is qualitatively different in lupus patients than it is in adults (James, J. A., et al., *Arthritis Rheum.*, 41:S308 (1998)). EBV infection tends to precede lupus in affected individuals.

Other autoimmune diseases, including both rheumatoid arthritis and Sjogren's syndrome, have been explored for a possible relationship to Epstein-Barr virus. See Fox R. I., et al. *J. Rheumatol.* 19:18-24 (1992). The evidence which they conclude supports a role for Epstein-Barr virus in rheumatoid arthritis includes: similarity between synovial and viral antigens, higher levels of antibodies against the Epstein-Barr virus Nuclear Antigens 1 and 3, and the lower ability of lymphocytes to prevent the outgrowth of autologous, Epstein-Barr virus infected lymphocytes (Fox, R. I. *Current Opin. Rheum.* 7:409-416 (1995)).

TABLE 1

Frequency of EBV-related, RAP or RANA antibodies by precipitation in RA patients and controls.

| Author (year) | RA | | controls | | | |
|---|---|---|---|---|---|---|
| | #pos/total | % | #pos/total | % | odds ratio | p-value |
| G Dalldorf (1969)[1] | 6/21 | 29% | 2/106 | 1.9% | 20.8 | 0.00001 |
| MA Alspaugh (1976)[2] | 69/141 | 49% | 6/71 | 8% | 10.41 | <0.00001 |
| MA Catalano (1979)[3] | 44/47 | 94% | 12/48 | 25% | 44 | <0.00001 |
| PB Ferrel (1981)[4] | 62/87 | 71% | 3/53 | 6% | 69 | <0.00001 |
| MA Alspaugh (1981)[5] | 44/61 | 72% | 1/16 | 6% | 39 | <0.00001 |
| PJW Venables (1981)[6] | 86/100 | 86% | 50/93 | 54% | 5.3 | <0.00001 |
| DA Bell (1984)[7] | 13/31 | 42% | 3/26 | 12% | 5.5 | 0.02 |
| K Nakabayashi[8] (1985) | 24/40 | 60% | 2/30 | 7% | 21 | <0.00001 |

[1]Dalldorf, G., et al., J. Amer. Med. Assn. 208: 1365-8 (1969)
[2]Alsbaugh, M. A. & Tan, E. M., Arthritis Rheum. 19: 711-9 (1976)
[3]Catalano, M. A., et al., Proc. Natl. Acad. Sci USA 76: 5825-8 (1979)
[4]Ferrel, P. B., et al., J. Clin. Invest. 67: 681-7 (1981)
[5]Alsbaugh, M. A., et al., J. Clin. Invest. 67: 1134-40 (1981)
[6]Venables, P. J. W., et al., Arthritis Rheum. 24: 1459-68 (1981)
[7]Bell, D. A. & Alsbaugh, M. A. J. Rheumatol. 11: 277-81 (1984)
[8]Nakabayashi, K., et al., Rheumatol. Int. 5: 61-7 (1985)

TABLE 2

Frequency of anti-RANA antibodies by immunofluoresence in RA patients and controls.

| Author (year) | RA | | controls | | | |
|---|---|---|---|---|---|---|
| | #pos/total | % | #pos/total | % | odds ratio | p-value |
| EM Tan (1979)[1] | 59/90 | 67% | 6/71 | 8% | 21 | <0.00001 |
| KC Ng (1980)[2] | 116/124 | 94% | 8/50 | 16% | 76 | <0.00001 |

[1]Tan, E. M. Rev. Inf. Dis. 1: 997-1006 (1979)
[2]Ng, K. C., et al., Lancet 1(8166): 447-9 (1980)

TABLE 3

Frequency of anti-EBNA-1 antibodies by immunofluoresence in RA patients and controls.

| | RA | | controls | | | |
| --- | --- | --- | --- | --- | --- | --- |
| Author (year) | #pos/total | % | #pos/total | % | odds ratio | p-value |
| MA Catalano (1979)[1] | 49/50 | 98% | 41/47 | 87% | 7.2 | 0.05 |
| KC Ng (1980)[2] | 55/64 | 86% | 36/50 | 72% | 2.4 | >0.05 |
| PB Ferrel (1981)[3] | 77/80 | 97% | 45/51 | 89% | 3.4 | >0.05 |
| A Kahan (1985)[4] | 47/47 | 100% | 14/14 | 100% | 1.0 | 1.0 |
| M Musiani (1987)[5] | 19/35 | 54% | 6/40 | 15% | 6.7 | <0.0001 |
| T Yokochi (1989)[6] | 18/22 | 82% | 2/14 | 14% | 27 | <0.00001 |

[1]Catalano, M. A., et al., Proc. Natl. Acad. Sci. USA 76: 5825-8 (1979)
[2]Ng, K. C., et al., Lancet 1(8166): 447-9 (1980)
[3]Ferrel, P. B., et al., J. Clin. Invest. 67: 681-7 (1981)
[4]Kahan, A., et al., Arthritis Rheum. 28: 961-70 (1985)
[5]Musaini, M., et al. Ann. Rheum. Dis. 46: 837-42 (1987)
[6]Yokochi, T., et al., J. Rheumatol. 16: 1029-32 (1989)

It has been proposed that Epstein-Barr virus is an etiologic agent for Sjogren's syndrome (Whittingham, S., et al. *Med. Hypothesis* 22:373-386 (1987)). They postulate that the combined effect of Epstein-Barr virus infection and autoimmunity leads to Sjogren's syndrome.

A higher level and frequency of Epstein-Barr virus, as well as other viruses, are found in salivary gland epithelium and gland tissue of patients with Sjogren's Syndrome (Fox, R.I. et al. *J. Immunol* 137:3162-3168 (1986)); (Fox, R. I. *Current Opin. Rheum.* 7:409-416 (1995)). Evidence for Epstein-Barr virus in 80% of the lacrimal gland specimens from Sjogren's syndrome patients and in none of the controls was reported by Pflugfelder, S. A. et al *Ophthalmology* 97:976-984 (1990); and Pflugfelder, S. A. et al. *Am. J. Pathol.* 143:49-64 (1993). Higher levels of hybridization between an Epstein-Barr virus DNA probe and the nuclei of salivary gland epithelial cells in Sjogren's syndrome than in controls was reported by Karameris, A. et al. *Clin. Exp. Rheum.* 10:327-332 (1992).

An increase in the Epstein-Barr virus production by B cells in patients with Sjogren's syndrome was described by Tateishi, M. et al. *Arthritis Rhuem.* 36:827-835 (1993). A minor increase in antibody levels against Epstein-Barr virus Nuclear Antigen-2 domains in Sjogren's syndrome compared to controls was published by Inoue, N. et al. *J. Infect. Dis.* 164;22-28 (1991). A modest elevation of anti-Epstein-Barr Nuclear antigen, anti-Early Antigen and anti-Epstein-Barr virus Viral Capsid Antigen (all measured by immunofluorescence) was described by Toda, I., et al. Sjogren's syndrome (SS) and Epstein-Barr virus (EBV) reactivation. In Lacrimal Gland, Tear Film, and Dry Eye Syndrome. D. A. Sullivan, ed. pp 647-650 (Plenum Press, New York 1994).

Others, however, found no such relationship and concluded that the frequency of Epstein-Barr virus DNA in salivary biopsy specimens was no different in patients with Sjogren's syndrome when compared with normal (Venables, P. J. W., et al. *Clin. Exp. Immunol.* 75:359-364 (1989); Venables, P. J. W., et al. *J. Autoimmunity* 2:439-438 (1989); Deacon, L. M., et al. *Am J. Med.* 92:453-454 (1992); Venables, P. J. W. et al. *Clin. Exp. Immunol.* 75:359-364 (1989); Maitland (Maitland, N.J. *Am. J. Med.* 96:97 (1994); Deacon, E. M., et al. *J. Pathol.* 163:351-360 (1991); Mariette, X., et al. *Am. J. Med.* 90:286-294 (1991).

An example of double infection with Epstein-Barr virus and another virus is found in a cell line isolated from a patient with apparent multiple sclerosis (Haahr, S. et al. *Ann. N. Y. Acad. Sci.* 724:148-156 (1996)). The increased prevalence of seroconversion among multiple sclerosis patients, relative to controls, has led to the suggestion that Epstein-Barr virus may be an etiologic agent in multiple sclerosis (Sumaya, C. V. et al. *Ann. Neurol.* 17:371-377 (1985); Bray, P. F., et al. *Arch. Neurol.* 40:406-408 (1983); Larsen. P. D., et al. *Neurology* 35:435-438 (1985); Warner, H. B. and Carp. R. I. *Med. Hypothesis* 25:93-97 (1988); Bray, P. F. et al. *Neurology* (1992)).

It is therefore believed that agents specifically targeted to latent viral proteins, especially EBV latent proteins, may be effective to reduce or treat diseases including autoimmune diseases such as SLE, Sjogren's Syndrome, rheumatoid arthritis, and Multiple Sclerosis.

Methods of Administration and Dosages

Therapy can be by inducing an immune response to the latent virus (vaccine), killing of the infected cells, or removal of infected cells. The antibody conjugated to a cytotoxic agent can also be used for immunotherapy to kill cells infected with a virus that is at least partly in the latent stage of its life cycle and is expressing the proteins of latency with epitopes reactive with the disclosed antibodies. Effective dosages of antibody conjugate will vary based upon affinity, selectivity and concentration of the antibody.

The dosage ranges for the administration of the antibody conjugates are those large enough to ameliorate the symptoms of the immune response mediated disorder, but low enough to avoid adverse side effects, such as unwanted cross-reactions or anaphylactic reactions. Generally, the dosage will vary with the age, condition, and extent of the disease in the patient and can be determined by one of skill in the art. The dosage can be adjusted by the individual physician in the event of any contraindications. Dosage can vary from one to multiple doses administered daily, for one to several days. Generally, when the antibodies of the invention are administered conjugated with therapeutic agents lower dosages, as compared those used for in vivo immunodiagnostic imaging, can be used.

In a preferred embodiment, the vaccine is administered in a dosage and on a schedule which elicits a response capable of either blocking primary EBV infection or significantly reducing the EBV load during primary infection, to avert clinical symptoms.

Vaccination

A protocol for vaccination to induce an immune response to the infected cells is designed based on standard techniques. Efficacy can be determined based on measurements of antibody titers to the latent viral proteins and using diagnostic techniques to determine the presence and/or number of infected cells remaining after treatment. Vaccination protocols range from a single immunization to multiple boosters. Priming vaccinations followed by boosters may be required, or it may be necessary to utilize a prolonged treatment protocol with low quantities of antigen, as is done with the treatment of allergies.

Diagnostic Uses

Labelled antibody conjugates can be used to confirm and/or quantitate the presence of a latent viral infection. It is also possible to determine whether a particular therapeutic regimen aimed at reducing the viral infection is effective.

The antibodies specifically binding to the latent viral antigens present on the surface of the cells infected with the virus can be used in assays with either liquid phase or solid phase carriers and with any of a variety of labels, in either competitive or noncompetitive assays and in either a direct or indirect format. Examples of such immunoassays are the radioimmunassay (RIA) and the sandwich (immunometric) assay. Immunoassays can be run in either the forward, reverse, or simultaneous modes, including immunohistochemical assays on physiological samples.

The extracellular portion of the targeted latent viral antigen is presented on the surfaces of cells. These cells can therefore be detected by the disclosed antibodies in biological fluids and tissues. Any sample containing a detectable amount of the extracellular portion of LMP-2A or a cell expressing the extracellular portion of LMP-2A can be used. Normally, a sample is a liquid such as saliva, cerebrospinal fluid, blood, or serum or a solid or semi-solid such as tissues.

In using the disclosed antibodies for the in vivo detection of the latent viral antigen, the detectably labeled monoclonal antibody is given in a dose which is sufficient to enable detection of cells which are latently infected with virus.

It is desirable that the detectably labeled antibody be rapidly cleared from the circulatory system in order to give the best target-to-background signal ratio. Typically, the dosage of antibody will vary from about 0.01 mg/m$^2$ to about 20 mg/m$^2$, preferably about 0.1 mg/m$^2$ to about 10 mg/m$^2$.

For in vivo diagnostic imaging using a radioisotope, the type of detection instrument available is a major factor in selecting a given radioisotope. The radioisotope chosen must have a type of decay which is detectable for a given type of instrument. Still another important factor in selecting a radioisotope for in vivo diagnosis is that the half-life of the radioisotope be long enough so that it is still detectable at the time of maximum uptake by the target, but short enough so that deleterious radiation with respect to the host is minimized. Ideally, a radioisotope used for in vivo imaging will lack a particle emission, but produce a large number of photons in the 140-250 keV range, which may be readily detected by conventional gamma cameras.

A preferred treatment is the use of viral proteins to vaccinate a patient against the virus. Peptides used as vaccines are preferably administered intramuscularly or subcutaneously. The dose, schedule of doses and route of administration may be varied, whether oral, nasal, vaginal, rectal, extraocular, intramuscular, intracutaneous, subcutaneous, or intravenous, to avoid autoimmunity and, yet, to achieve immunity from Epstein-Barr virus infection.

The response to the unmodified vaccine may be further influenced by its composition. The particular adjuvant employed (its concentration, dose and physical state), concentration of the virus in the vaccine, and treatment of the unmodified vaccine with physical environmental changes, for example, temperature and pressure, the particular buffer, and the particular preservative(s) (if any) will be selected to reduce the likelihood of developing an autoimmune disorder, for example using the animal strains discussed below. This same or different vaccine may be useful in reducing or eliminating the effect of an existing latent or active Epstein-Barr virus infection upon autoimmunity.

Methods for Administration

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

The present invention will be further understood by reference to the following non-limiting examples.

EXAMPLE 1

Preparation of Anti-Latent EBV Antibodies.

To generate an *E. coli* LMP-2A expression plasmid, a 1,029 bp SalI/NsiI fragment was removed from the LMP-2A cDNA clone (obtained from Dr. Mike Kurilla, formerly from the Department of Pathology, University of Virginia Health Sciences Center) (FIG. 1). This fragment of LMP-2A cDNA corresponds to bp 789-1817 of the GenBank LMP-2A entry (Accession #M24212) and encodes amino acids 259-497 of LMP-2A as well as some of the 3' untranslated sequence. The fragment was ligated into SalII/Pstl digested pMal-C2 (New England Biolabs, Beverely, Mass.). The resulting construct encodes a maltose binding protein (MBP) LMP-2A fusion protein (construct #1). Separating the maltose binding protein and LMP-2A is a run of 20 arginines and a Factor Xa cleavage site. The Factor Xa cleavage site allows the LMP-2A peptide fragment to be separated and isolated from the maltose binding protein moiety.

A second construct was generated by cloning a 1,760 bp BamHI/NsiI fragment from the LMP-2A cDNA clone and ligated into BamHI/Pstl digested pMal-C2. To maintain the proper open reading frame the new plasmid was digested with BamII and XmIII, blunt-ended with the Klenow DNA polymerase I fragment, and re-ligated. The resulting plasmid encodes nearly the entire full-length LMP-2A protein (a.a. 18-498). In fact, amino acids 1-14 encode the signal sequence. Thus, this construct encodes all but the first four amino acids of the mature peptide. The resulting construct encodes a MBP-full length LMP-2A fusion protein. *E. coli* cells transfected with the LMP-2A fusion protein construct appeared to express a full-length protein. This was based on the presence of a 93,000 molecular weight protein on SDS-PAGE and Western blot detection using rabbit anti-MBP polyclonal sera. However, over 90% of the protein expressed from this construct appeared to be native maltose binding protein (from affinity purification with an amylose resin column). This could have been due to proteolysis, instability of the fusion protein, or premature translational termination. Because of the instability of the full-length LMP-2A fusion protein anti-LMP-2A antibodies were generated using the more stable and higher expressed truncated LMP-2A fusion protein.

A third LMP-2A construct was generated by cloning a SalI/HindIII fragment from the pMal-truncated LMP-2A fusion protein plasmid (construct #1). This fragment was cloned into the pQE9 expression vector (Qiagen). This vector expresses the truncated LMP-2A peptide with an N-terminal six His tag. Which can be used for affinity purification on a nickel column. This fragment has a molecular weight of 27,000 and the only additional amino acids are the six N-terminal histidine residues.

*E. coli* cells transfected with the truncated MBP-LMP-2A fusion protein plasmid (construct #1) expressed the MBP-LMP-2A fusion protein (FIG. 2). This was based on the presence of a 69,000 molecular weight protein on SDS-PAGE and Western blot detection using rabbit anti-MBP polyclonal sera. The LMP-2A fusion protein encodes 212 amino acids of the transmembrane domains and the C-terminal 27 amino acids, which are intracellular, as opposed to the 351 amino acids in the mature protein.

MBP-LMP2A fusion protein was isolated from *E. coli* cells that had been induced by the addition of IPTG to 0.3 mM for 2 hours at 37 C. Cells were harvested by centrifugation and lysed by sonication. The MBP-LMP2A fusion protein was isolated from the cell lysate by affinity chromatography using amylose resin. Bound MBP-LMP-2A was eluted from the column using 10 mM Maltose.

EXAMPLE 2

Immunization of Animals.

Immunizations were performed as follows: On day one, two New Zealand White rabbits were immunized with 500 mcg recombinant MBP-LMP-2A fusion protein (in 0.5 ml PBS) emulsified in 0.5 ml complete Freunds adjuvant and injected by intraperitoneal and subcutaneous routes. On days 28, 56, and 100 the animals were boosted with another 500 mcg of antigen in incomplete Freunds adjuvant. Pre-bleeds and weekly bleeds following the initial immunization were collected by ear puncture to determine the titer of anti-LMP-2A antibodies.

Western blot analysis showed that both the 55 kD wild-type LMP2A and Factor Xa released truncated LMP-2A were bound by antibodies from the animal immunized with MBP-truncated LMP-2A fusion protein (construct #1). Sera from the immunized animal was diluted 1:100 and incubated with a nictrocelluose membrane which had SDS-PAGE separated proteins electrophoretically transferred to the membrane. The bound rabbit antibodies were detected using goat anti-rabbit alkaline phosphatase conjugated antibodies. These results showed that rabbits immunized with the MBP truncated LMP-2A fusion protein generated antibodies that recognize LMP-2A.

Sera from immunized rabbits were also used in flow-cytometry experiments. Cell lines tested included EBV-transformed human B cells and murine L cells transiently transfected with a pCDNA-3 plasmid expressing the full-length LMP-2A cDNA under control of the CMV promoter. One microliter of rabbit sera was incubated with $1\times10^6$ cells in 40 microliters PBS. Cells were washed with PBS supplemented with to 1% BSA twice and incubated with FITC labeled goat anti-rabbit IgG and washed twice again. Labeled cells were visualized using a FacScan flow cytometer.

Two separate flowcytometry experiments showed that the rabbits immunized with the MBP-truncated LMP-2A fusion protein generated antibodies that recognize cells expressing LMP-2A. Pre-immune sera did not bind to human B cells infected with EBV. However, sera from immunized rabbits did. In addition, antibodies from the immunized sera did not bind to mouse L cells transfected with pCDNA3 vector alone. However, antibodies from the immunized sera did bind to mouse L cells transfected with the pCNDA3 vector containing the LMP-2A cDNA. These results showed that at least a population of the anti-LMP-2A antibodies recognized cells surface expressed LMP-2A.

Proteins were prepared from the known sequence of LMP-2A and were used to immunize rabbits. The results indicate that a variety of these antibodies bind extracellular portions of LMP-2A. Cells that express LMP-2A are bound by antibody to LMP-2A. Control cells do not express LMP-2A and are not bound by the antibodies to LMP-2A.

Epstein-Barr virus, as well as most of the other human herpesviruses, is limited to infection of only the human host. Non-primate animal species do not have the necessary complement receptor function to allow EBV infection. Also, other primates have their own variants of gamma herpes viruses. Since lower animals are not infected with EBV, they are not normally exposed to LMP-2A and no antibodies are usually made.

Balb/c mice were immunized with the same LMP-2A construct outlined above (construct #1). Balb/c mice were also immunized with a 6-Histidine-tagged LMP-2A (construct #3). These mice have mounted a significant immune response to LMP-2A. Over 500 hybridomas were generated from mice immunized with truncated LMP-2A and screened by ELISA for LMP-2A specificity. Three clones were identified that contained the desired specificity (bound LMP-2A fusion protein but not Maltose binding protein control).

This data is predictive of results with other latent proteins such as LMP-2B. LMP-2B differs from LMP-2A in the cytoplasmic portion of the molecule. Consequently, a similar availability of the extracellular portions of these two molecules is predicted.

We claim:

1. A composition comprising a molecule that specifically binds an extracellular portion of the latent viral membrane bound protein of EBV expressed in the latent viral membrane in the latent life cycle, wherein the molecule is coupled to a detectable label, cytotoxic agent or solid support.

2. The composition of claim 1 wherein the expressed Epstein-Barr virus protein or fragment thereof is selected from the group consisting of LMP-1, LMP-2A, LMP-2B, LP peptides presented in HLA, and EBNA peptides presented in HLA.

3. The composition of claim 1 wherein the expressed Epstein-Barr virus protein is selected from the group consisting of the LMP-2A or LMP-2B proteins.

4. The composition of claim 3 wherein the molecule binds the portion of LMP-2A from amino acids 259 to 497 or of LMP-2B from amino acids 140 to 378, both SEQ ID NO: 1.

5. The composition of claim 1 wherein the molecule is an antibody.

6. The composition of claim 1 wherein the molecule is a peptide.

7. The composition of claim 1 wherein the molecule is a chemical.

* * * * *

UNITED STATES PATENT AND TRADEMARK OFFICE
CERTIFICATE OF CORRECTION

PATENT NO. : 7,410,642 B2  Page 1 of 1
APPLICATION NO. : 11/405355
DATED : August 12, 2008
INVENTOR(S) : John B. Harley et al.

It is certified that error appears in the above-identified patent and that said Letters Patent is hereby corrected as shown below:

In claim 2, column 27, line 41, delete "or fragment thereof".

In claim 3, column 28, line 32, delete "claim 1" and insert --claim 2-- therefor.

Delete claim 7, column 28, lines 43-44.

Signed and Sealed this

Nineteenth Day of January, 2010

David J. Kappos
*Director of the United States Patent and Trademark Office*

UNITED STATES PATENT AND TRADEMARK OFFICE
CERTIFICATE OF CORRECTION

PATENT NO.         : 7,410,642 B2                                                          Page 1 of 2
APPLICATION NO.    : 11/405355
DATED              : August 12, 2008
INVENTOR(S)        : John B. Harley et al.

It is certified that error appears in the above-identified patent and that said Letters Patent is hereby corrected as shown below:

Delete the title page and substitute therefore the attached title page showing the corrected number of claims in printed patent.

In claim 2, column 27, line 41, delete "or fragment thereof".

In claim 3, column 28, line 32, delete "claim 1" and insert --claim 2-- therefore.

Delete claim 7, column 28, lines 43-44.

This certificate supersedes the Certificate of Correction issued January 19, 2010.

Signed and Sealed this

Ninth Day of February, 2010

David J. Kappos
*Director of the United States Patent and Trademark Office*

(12) United States Patent
Harley et al.

(10) Patent No.: US 7,410,642 B2
(45) Date of Patent: Aug. 12, 2008

(54) ASSAYS AND THERAPIES FOR LATENT VIRAL INFECTION

(75) Inventors: John B. Harley, Oklahoma City, OK (US); Judith Ann James, Edmond, OK (US); Kenneth M. Kaufman, Oklahoma City, OK (US)

(73) Assignee: Oklahoma Medical Research Foundation, Oklahoma City, OK (US)

( * ) Notice: Subject to any disclaimer, the term of this patent is extended or adjusted under 35 U.S.C. 154(b) by 0 days.

(21) Appl. No.: 11/405,355

(22) Filed: Apr. 17, 2006

(65) Prior Publication Data

US 2006/0257427 A1    Nov. 16, 2006

Related U.S. Application Data

(62) Division of application No. 10/646,132, filed on Aug. 22, 2003, now Pat. No. 7,078,173, which is a division of application No. 09/718,693, filed on Nov. 22, 2000, now Pat. No. 6,642,008.

(60) Provisional application No. 60/167,212, filed on Nov. 24, 1999.

(51) Int. Cl.
*A61K 39/12* (2006.01)

(52) U.S. Cl. ............... 424/204.1; 424/130.1; 435/345

(58) Field of Classification Search ............... 435/435, 435/6; 424/204.1, 130.1
See application file for complete search history.

(56) References Cited

U.S. PATENT DOCUMENTS

| | | | |
|---|---|---|---|
| 4,244,946 A | 1/1981 | Rivier et al. | 514/15 |
| 4,305,872 A | 12/1981 | Johnston et al. | 530/330 |
| 4,316,891 A | 2/1982 | Guillemin et al. | 514/11 |
| 4,675,382 A | 6/1987 | Murphy | 530/350 |
| 4,792,525 A | 12/1988 | Ruoslahti et al. | 435/402 |
| 5,637,454 A | 6/1997 | Harley | 435/5 |
| 5,861,240 A * | 1/1999 | Ganem et al. | 435/5 |
| 5,906,820 A | 5/1999 | Bacha | 424/183.1 |

FOREIGN PATENT DOCUMENTS

| | | |
|---|---|---|
| WO | WO 98/30586 | 7/1998 |
| WO | WO 99/02550 | 1/1999 |

OTHER PUBLICATIONS

Rowe et al. Journal of General Virology, 1987, vol. 68, pp. 1575-1586.*
Meij et al. The Journal of Infectious Diseases, May 1999, vol. 179, pp. 1108-1115.*
Adelstein et al., "Radiobiologic implications of the microscopic distribution of energy from radionuclides," *Nucl. Med. Biol.*, 14:165-169, 1987.
Alford, Antiviral agents and viral diseases of man, 2nd ed. Raven Press: New York, pp. 433-486, 1984.
Alspaugh et al., "Elevated levels of antibodies to Epstein-Barr virus antigens in sera and synovial fluids of patients with rheumatoid arthritis," *J. Clin. Invest.*, 67:1134-1140, 1981.
Alspaugh et al., "Serum antibody in rheumatoid arthritis reactive with a cell-associated antigen. Demonstration by precipitation and immunofluorescence," *Arthr. Rheum.*, 19:711-719, 1976.
Ashley et al., "Detection of asymptomatic herpes simples virus infections after vaccination," *J. Virol.*, 61:253-258, 1987.
Babcock et al., "Epstein-barr virus-infected resting memory B cells, not proliferating lymphoblasts, accumulate in the peripheral blood of immunosuppressed patients," *J. Exp. Med.*, 190:567-576, 1999.
Barnes, *J. Pharma Weekly*, 1:11, 1995.
Bell et al., "Antibody to rheumatoid arthritis associated nuclear antigen (RANA) in familial rheumatoid arthritis," *J. Rheumatol.*, 11:277-281, 1984.
Bray et al., "Antibodies against Epstein-Barr Nuclear Antigen (EBNA) in Multiple Sclerosis CSF, and two pentapeptide sequence identities between EBNA and Myelin basic protein," *Arch. Neur.*, 42:1798-1804, 1992.
Bray et al., "Antibodies against Epstein-Barr nuclear antigen (EBNA) in multiple sclerosis CSF< and two pentapeptide sequences identities between EBNA and myelin basic protein," *Arch. Neur.*, 40:406-408, 1983.

(Continued)

*Primary Examiner*—Ali R. Salimi
(74) *Attorney, Agent, or Firm*—Fulbright & Jaworski, LLP

(57) ABSTRACT

Compositions that bind viral proteins that are specifically expressed during the latent stage of the viral life cycle are disclosed. These compositions bind the latent viral proteins while the viral proteins are expressed in their cellular host, and provide a means for targeting cells that harbor latent virus. In a preferred embodiment the compositions are antibodies which bind the extracellular region of the latent viral protein, most preferably LMP-2A, an EBV latent protein, which are conjugated to a diagnostic or cytotoxic agent or immobilized to a solid support for removal of the infected cells. These antibodies are capable of distinguishing cells expressing EBV DNA from cells which are not expressing EBV DNA. Compositions that can be used to elicit production of these antibodies, or as a vaccine, are also disclosed. Methods for generating diagnostic or cytotoxic reagents and vaccines based on the viral epitopes that identify cells harboring latent virus are also disclosed. The antibody conjugates can be used in diagnostic assays to identify cells expressing latent viral protein and people who are harboring latent viral particles. The antibody conjugates can also be used to remove the infected cells or to kill the infected the cells. Alternatively, or in addition, the viral proteins or portions thereof can be used as a vaccine to induce an immune reaction by the host to kill the infected cells. These methods can be used to detect or treat patients harboring latent viruses like EBV and who are at risk of developing a disease such as an autoimmune disease like systemic lupus erythematosus (SLE) and rheumatoid arthritis (RA).

6 Claims, No Drawings